(12) United States Patent
Schmidt et al.

(10) Patent No.: US 6,599,921 B2
(45) Date of Patent: Jul. 29, 2003

(54) NON-STEROIDAL ESTROGEN RECEPTOR LIGANDS

(75) Inventors: Jonathan Martin Schmidt, Elora (CA); Julie Mercure, Guelph (CA); Jeffry Lawrence Lowell, Lexington, KY (US); Stefan Kwiatkowski, Lexington, KY (US); Krzysztof Pupek, Woodrigh, IL (US); Shuguang Zhu, Seattle, WA (US); John Whelan, Toronto (CA); Natalie Lazarowych, Richmond Hill (CA)

(73) Assignee: NanoDesign, Inc., Montreal (CA)

( * ) Notice: Subject to any disclaimer, the term of this patent is extended or adjusted under 35 U.S.C. 154(b) by 0 days.

(21) Appl. No.: 09/934,254

(22) Filed: Aug. 21, 2001

(65) Prior Publication Data

US 2002/0156077 A1 Oct. 24, 2002

Related U.S. Application Data

(60) Provisional application No. 60/270,145, filed on Feb. 22, 2001.

(51) Int. Cl.$^7$ ..................... A61K 31/445; C07D 211/06

(52) U.S. Cl. ................... 514/325; 514/425; 514/651; 546/203; 548/528; 564/317

(58) Field of Search ................. 514/325, 428, 514/651; 546/203; 548/528; 564/317

(56) References Cited

U.S. PATENT DOCUMENTS

| | | | |
|---|---|---|---|
| 5,393,785 A | 2/1995 | Labrie et al. | 514/622 |
| 5,395,842 A | 3/1995 | Labrie et al. | 514/620 |
| 5,552,412 A | 9/1996 | Cameron et al. | 514/317 |
| 5,589,500 A | 12/1996 | Edwards et al. | 514/428 |
| 5,631,249 A | 5/1997 | Labrie et al. | 514/182 |
| 5,641,790 A | 6/1997 | Draper | 514/333 |
| 5,650,425 A | 7/1997 | Biegnon et al. | 514/408 |
| 5,681,835 A | 10/1997 | Willson | 514/237.5 |
| 5,686,465 A | 11/1997 | Labrie et al. | 514/320 |
| 5,733,902 A | 3/1998 | Schneider | 514/177 |

FOREIGN PATENT DOCUMENTS

EP       0818453       1/1998

OTHER PUBLICATIONS

Campeta et al. "Identification of photodegradants of droloxifene . . . . . " CA 132:269944 (1999__.*
Schneider et al. "hydroxy substituted 10–ethyl–9–phenylpenathrenes . . . . . " CA 107:96415 (1987).*
Anstead et al., "The estradiol pharmacophore: Ligand structure—estrogen receptor binding affinity relationships and a model for the receptor binding site," Steriods, 62:268–303, 1997.

DeFriend et al., "Investigation of a new pure antiestrogen (ICI 182780) in women with primary breast cancer," Cancer Res., 54(2):408–414, 1994.
England and Jordan, "Pure antiestrogens as a new therapy for breast cancer," Oncology Res., 9:397–402, 1997.
Fisher et al., "Tamoxifen for prevention of breast cancer: report of the national surgical adjuvant breast and bowel project P–1 study," J. of the Nat'l Cancer Institute, 90(18):1371–1388, 1998.
Gradishar and Jordan, "Clinical potential of new antiestrogens," J. of Clinical Oncology, 15(2):840–852, 1997.
Grese et al., "Synthesis and pharmacology of conformationally restricted raloxifene analogues: highly potent selective estrogen receptor modulators," J. Med. Chem., 41:1272–1283, 1998.
Grundy, "Artificial estrogens," Chem. Rev., 57:281–416, 1957.
Howell et al., "Response to a specific antioestrogen (ICI 182780) in tamoxifen–resistant breast cancer," Lancet, 345:29–30, 1995.
Jordan and Murphy, "Endocrine pharmacology of antiestrogens as antitumor agents," Endocrine Reviews, 11(4):578–611, 1990.
Josefson, "Breast cancer trial stopped early," BMJ, 316:1185, 1998.
LaBudde and Heidelberger, "The synthesis of the mono– and dihydroxy derivatives of 1,2,5,6–dibenzanthracene excreted by the rabbit and of other hydroxylated dibenzanthracene derivatives," Synthesis of Hydroxylated Dibenzanthracene, 80:1225–1236, 1958.
Lerner and Jordan, "Development of antiestrogens and their use in breast cancer: Eighth Cain Memorial Award Lecture," Cancer Res., 50:4177–4189, 1990.
Levenson and Jordan, "The key to the antiestrogenic mechanism of raloxifene is amino acid 351 (Aspartate) in the estrogen receptor," Cancer Res., 58:1872–1875, 1998.
McDonnell et al., "Cellular mechanisms which distinguish between hormone– and antihormone–activated estrogen receptor," Annals New York Academy of Sciences, 761:121–137, 1995.
Mitlak and Cohen, "In search of optimal long–term female hormone replacement: the potential of selective estrogen receptor modulators," Horm Res., 48:155–163, 1997.
Nicholson et al., "Pure antiestrogens. The most important advance in the endocrine therapy of breast cancer since 1896?" Annals New York Academy of Science, 784:325–335, 1996.

(List continued on next page.)

Primary Examiner—Ceila Chang
(74) Attorney, Agent, or Firm—Fulbright & Jaworski

(57) ABSTRACT

Novel non-steroidal estrogen receptor ligands and methods of synthesis are disclosed. The novel molecules are intended for use in therapeutic preparations for the treatment of estrogen receptor related disease states. The compounds specified are tetra-cyclic derivatives and have been shown to be antiproliferative against human estrogen-dependent cancer cells and to have good binding affinity for the estrogen receptor.

22 Claims, 2 Drawing Sheets

OTHER PUBLICATIONS

Nicholson, "Antioestrogens and breast cancer therapy," *Bailliere Tindall,* 60–86, 1987.

Parczyk and Schneider, "The future of antihormone therapy: innovations based on an established principle," *J. Cancer Res. Clin Oncol.,* 122:383–396, 1996.

Powles, "Tamoxifen as a cancer treatment drug (anticarcinogen). Efficacy of tamoxifen as treatment of breast cancer," *Seminars in Oncology,* 24(1), Supp. 1: S1–48—S1–54, 1997.

Rauschning and Pritchard, "Droloxifene, a new antiestrogen: its role in metastatic breast cancer," *Breast Cancer Res. And Treatment,* 31:83–94, 1994.

Wakeling and Bowler, "Biology and mode of action of pure antioestrogens," *J. Steroid Biochem.,* 30(1–6):141–147, 1988.

Wakeling and Bowler, "ICI 182,780, a new antioestrogen with clinical potential," *J. Steroid Biochem. Molec. Biol.,* 43(1–3):173–177, 1992.

Wakeling and Bowler, "Novel antioestrogens without partial agonist activity," *J. Steroid Biochem.,* 31(48):645–653, 1988.

Wakeling and Bowler, "Steroidal pure antioestrogens," *J. Endocr.,* 112:R7–R10, 1987.

Wakeling et al., "A potent specific pure antiestrogen with clinical potential," *Cancer Res.,* 51:3867–3873, 1991.

Wakeling, "The future of new pure antiestrogens in clinical breast cancer," *Breast Cancer Res. And Treatment,* 25:1–9, 1993.

Wakeling, "Therapeutic potential of pure antioestrogens in the treatment of breast cancer," *J. Steroid Biochem. Molec. Biol.,* 17(6):771–775, 1990.

* cited by examiner

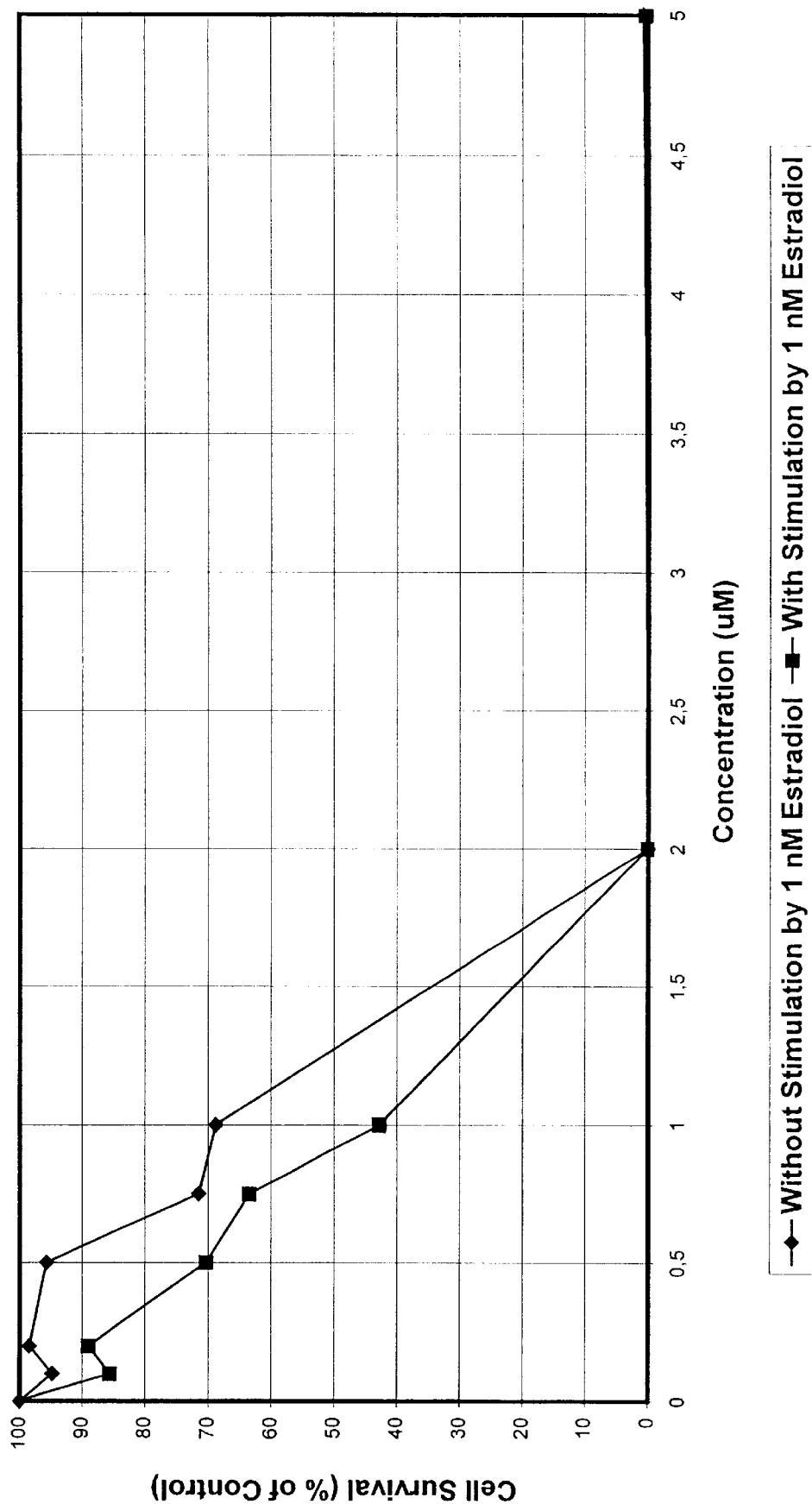

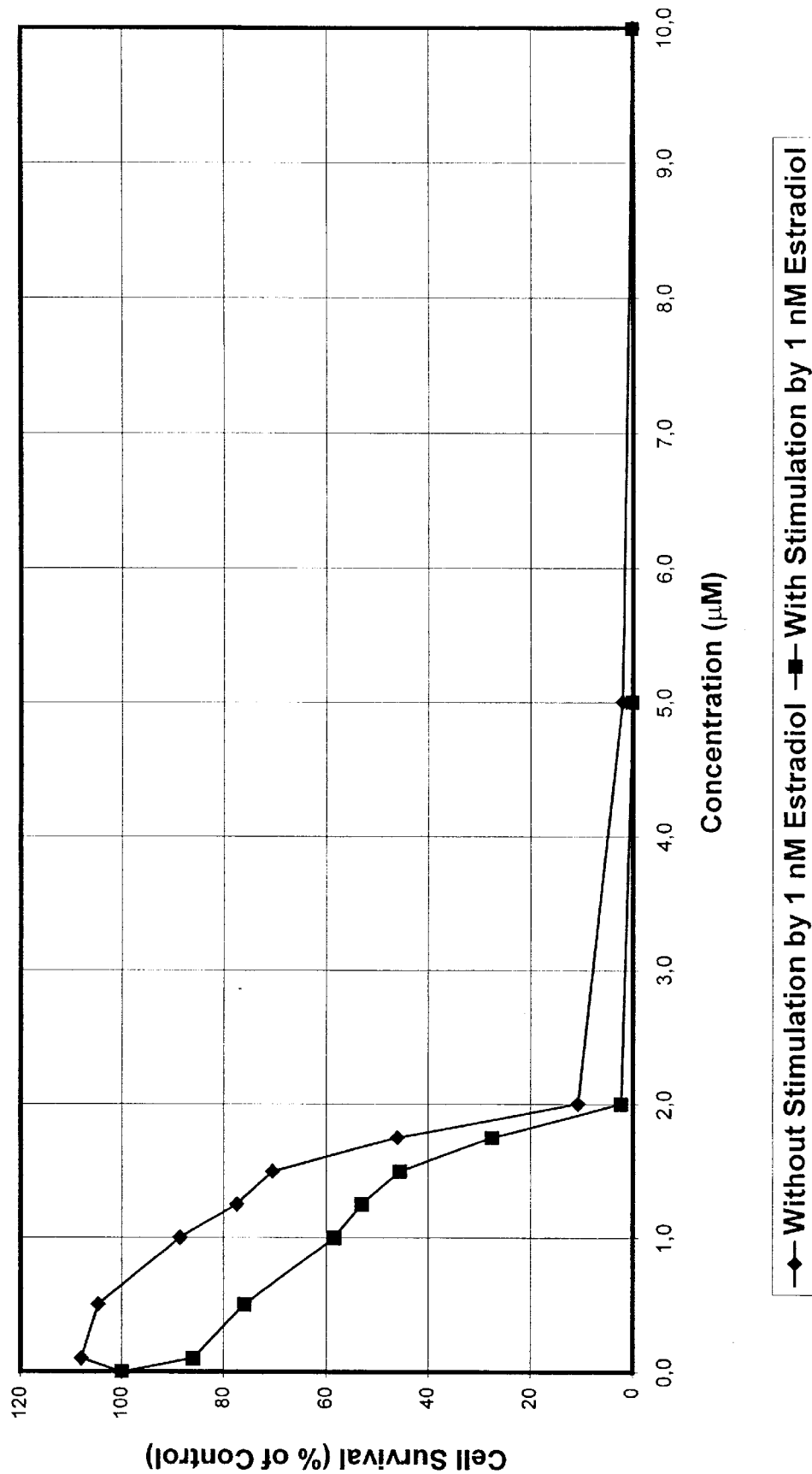
Figure 2: MCF-7 Cell Proliferation Assay Results for Compound of Formula 4

NON-STEROIDAL ESTROGEN RECEPTOR LIGANDS

This application claims priority to pending provisional patent application Ser. No. 60/270,145, filed Feb. 22, 2001.

FIELD OF THE INVENTION

The present invention relates to non-steroidal compounds that demonstrate high-binding affinity for the estrogen receptor, while being devoid of any agonistic effects on reproductive tissues and to non-steroidal compounds that have a high binding affinity for the estrogen receptor while also having some agonistic activity specific to the skeletal and cardiovascular systems. More particularly, the present invention relates to novel non-steroidal ligands for the estrogen receptor as well as methods of making the same and their applications in treating a variety of disease states.

BACKGROUND OF THE INVENTION

Interfering with the activity of endogenously produced estrogens can modulate the course of many estrogen-dependent diseases. One approach has been to prevent estrogen biosynthesis using inhibitors of aromatase enzymes, which are responsible for the conversion of androgens to estrogens. Alternatively, estrogen activity may be interrupted at the receptor level using estrogen antagonists.

The involvement of estrogens in the development and progression of breast cancer has been known for over 100 years. In normal breast tissue, only 6% of the mammary epithelial cells express estrogen receptors (McDonnell et al., *Ann. N. Y. Acad. Sci.* 1996; 121–37), whereas over 60% of primary breast tumors are estrogen receptor positive and are dependent on estrogen for growth. However, it has been documented that other agents (e.g. growth factors) can activate estrogen receptors in the absence of estrogen (Pareczyk and Schneider, *J. Cancer Res. Clin. Oncol.* 1996; 122:383–96). As a result, blocking activity at the estrogen receptor is potentially a more effective therapeutic strategy than inhibition of estrogen biosynthesis.

Tamoxifen, a triphenylethene derivative, is the most widely used anti-estrogen for the treatment of breast cancer. It is predominantly used as a first-line therapy in metastatic breast cancer to prolong survival. Unfortunately, resistance to tamoxifen usually develops within 15 months of therapy initiation. Nevertheless, the clinical efficacy of tamoxifen as a hormonal therapy for many types of breast cancer has led to the search for more potent estrogen receptor antagonists.

Several new antiestrogens including toremifene, droloxifene, idoxifene, TAT-59 and raloxifene are currently being evaluated in the laboratory and in the clinic for the treatment of estrogen related disorders (Gradishar and Jordan, *J. Clin. Oncol.* 1997; 15(2):840–52). There has been considerable concern regarding the long-term use of tamoxifen due to an increase in incidences of endometrial cancer, deep venous thrombosis and pulmonary embolism for patients receiving the therapy (Rauschning and Pritchard, *Breast Cancer Res. Treat* 1994; 31:83–94). Other more common side effects include, hot flushes, vaginal bleeding and blurred vision (Nicholson R I, *Bailliere and Tindall*, 1987:60–87). Despite these side effects, results from one clinical study have demonstrated the utility of tamoxifen in the prevention of breast cancer in women at high risk of developing the disease (Fisher et al, *J. of the Nat'l Cancer Inst.* 1998; Vol. 90; No. 18; 1371–1388). The FDA has approved tamoxifen for use as a prophylactic.

It has been suggested that the partially agonistic properties of some anti-estrogens are responsible for both their side-effect profile and the development of resistance to therapy (Nicholson et al., *Ann. N. Y. Acad. Sci.* 1996; 784:-325–35). Partial agonists are compounds for which the balance in the expression of antagonistic and agonistic activity depends on the dose administered, as well as on the species and target organ studied. More specifically, differences in agonistic/antagonistic responses depend on the presence of cell-specific proteins that can act as co-activators or transcription factors (Mitlak and Cohen, *Horm. Res.* 1997; 48:155–63). In vitro and in vivo experiments have suggested that the agonistic properties of some anti-estrogens may become dominant through the course of therapy. This has been demonstrated in clinical settings where 10–30% of tamoxifen-resistant patients showed improvement of their diseases after withdrawal from tamoxifen therapy (Parczyk and Schneider, *J. Cancer Res. Clin. Oncol.* 1996; 122:383–96).

"Pure" anti-estrogens are compounds that have exclusively antagonistic properties and lead to the formation of inactive ligand-receptor complexes. In contrast to partial agonists that stimulate the expression of estrogen receptors, pure anti-estrogens cause a down-regulation of cellular receptor protein levels (Parczyk and Schneider, *J. Cancer Res. Clin. Oncol.* 1996; 122:383–96). Since the estrogen receptor is activated through estrogen-independent factors, the reduction in estrogen receptor levels obtained with pure anti-estrogens may offer clinical advantages over partial agonists and aromatase inhibitors. Clinical trials with pure anti-estrogens have shown efficacy against tamoxifen-resistant breast cancers where approximately two-thirds of tamoxifen-resistant patients responded to ICI 182780 (faslodex), and no significant adverse effects were observed (England and Jordan, *Oncol. Res.* 1997; 9:397–402).

Many studies performed to date have suggested that anti-estrogens with partial agonistic activity have positive effects on cardiovascular and skeletal systems. For example, tamoxifen lowers total and LDL cholesterol, lowers lipoprotein (A) and preserves bone mass in postmenopausal women undergoing breast cancer treatment (Mitlak and Cohen, *Horm. Res.* 1997; 48:155–63). Estrogens play an important role in the regulation and synthesis of lipids and therefore have a protective effect on the cardiovascular system. Following menopause, the risk of developing atherosclerosis and coronary disorders dramatically increases in women not undergoing hormone replacement therapy. In addition, estrogens are critically important in the maintenance of proper bone mass. As the circulating level of estrogen decreases, post-menopausal women experience an increase in the rate of bone turnover, resulting in net bone loss. Therefore, the positive effects of tamoxifen observed on skeletal and cardiovascular systems may be related to agonistic activity through the estrogen receptor present in those tissues (Mitlak and Cohen, *Horm. Res.* 1997; 48:155–63).

Other partial agonists currently in development have demonstrated anti-estrogenic effects on reproductive tissues with increased protective effects or estrogenic activity on the skeletal and cardiovascular systems. These compounds are known as Selective Estrogen Receptor Modulators (SERMs). Examples of these include droloxifene, which is being developed as an anti-osteoporotic agent, and raloxifene, which has been approved by the FDA for prevention of osteoporosis in post-menopausal women.

Although anti-cancer agents fall into specific classifications, it is not uncommon for agents to act by multiple modes of action. For example, tamoxifen has been shown to have anti-proliferative activity on cancer cells and endothelial cells by an estrogen independent mechanism. Taxol, an anti-mitotic agent acting on microtubules has also demonstrated anti-angiogenic properties, possibly by inducing apoptosis through Bcl-2 phosphorylation. These are but a few examples and the fact that some anti-estrogens have demonstrated anti-angiogenic properties is of particular interest to many in this field of research. Such a possibility is not precluded in the present invention.

There thus remains a need to develop a series of non-steroidal compounds that demonstrate high-binding affinity for the estrogen receptor, while being devoid of any agonistic effects on reproductive tissues. Alternatively, non-steroidal compounds that have a high binding affinity for the estrogen receptor and have some agonistic activity specific to the skeletal and cardiovascular systems are also desirable. Therefore, either pure anti-estrogens or partial anti-estrogens with high binding affinity, low toxicity and prolonged efficacy would be of great benefit.

The present invention seeks to meet these and other needs.

The present description refers to a number of documents, the content of which is herein incorporated by reference in their entirety.

SUMMARY OF THE INVENTION

It has now been discovered that certain novel estrogen binding ligands that have been shown to be anti-proliferative against human estrogen-dependent cancer cells and having a high binding affinity for the estrogen receptor can be constructed as set forth herein.

In one embodiment, the present invention relates to a series of non-steroidal compounds that demonstrate high-binding affinity for the estrogen receptor, while being devoid of any agonistic effects on reproductive tissues.

In another embodiment, the present invention also relates to either pure anti-estrogens or partial anti-estrogens with high binding affinity, low toxicity and prolonged efficacy.

In yet another embodiment, the present invention relates to non-steroidal anti-estrogens based on the tetra-cyclic derivatives described herein and as described in their synthetic pathways.

In addition, in another embodiment the present invention seeks to provide non-steroidal anti-estrogens having good affinity for estrogen receptors.

In accordance with another embodiment, the present invention seeks to provide a therapeutic anti-estrogen composition useful in the treatment of estrogen-related diseases. These diseases include, but are not limited to breast cancer, uterine cancer, ovarian cancer, osteoporosis, cardiovascular diseases, premenstrual syndrome, uterine fibroma, endometriosis, precocious puberty, vasomotor symptoms associated with menopause, atrophic vaginitis, CNS disorders (including Alzheimer's), infertility, glaucoma and elevated serum cholesterol.

The above and other embodiments are accomplished by providing a pharmaceutical composition comprising a therapeutically effective amount of an anti-estrogen specified herein. As used herein, the terms $R^1$, $R^2$, $R^3$, $R^4$ and $R^5$ refer to substituents whose location on the tetra-cyclic skeleton is illustrated as depicted in Formula 1 below:

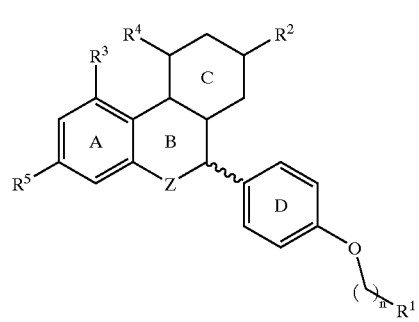

Formula 1 and wherein the A and D rings are always aromatic.

Certain preferred substituents include, but are not limited to the following:

Z is C (carbon) where the B-ring and C-ring are aromatic. Alternatively where Z is carbon, the B-ring may be unsaturated and the C-ring aromatic. In another embodiment where Z is carbon, the B-ring is aromatic and the C-ring is unsaturated. In all embodiments where Z is carbon the $R^1$, $R^2$, $R^3$, $R^4$, and $R^5$ substituents are as described below. Z can also be either O (oxygen) or S (sulfur) in an alternate embodiment in which case the B-ring is not aromatic, but the C-ring may or may not be aromatic and $R^1$ to $R^5$ are as described below.

Certain preferred substituents for $R^1$ include, but are not limited to 1-pyrrolidinyl or 1-piperidinyl, methyl-1-pyrrolidinyl, dimethyl-1-pyrrolidino, 4-morpholino, dimethylamino, diethylamino, diisopropylamino, or 1-hexamethyleneimino and n is an integer from 1 to 4. The nitrogen atom contained in the pyrrolidine and piperidine functional groups is expected to be predominantly protonated at physiological pH.

The preferred orientation of the bond linking the B and D rings is as shown below in Formula 2. The wedged line indicates the preferred configuration.

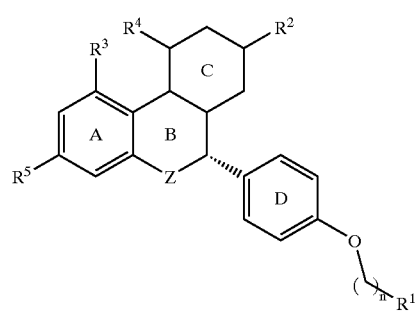

Formula 2

It has been documented that a correctly positioned alkylaminoethoxy side chain may be required for anti-estrogenic activity (Levenson and Jordan, *Cancer Res.* 1998; 58:1872–75). Compounds containing such a side chain positioned in an orthogonal orientation as shown in Formula 1, relative to a tetracyclic steroid-like skeleton, have demonstrated full antagonistic activity on uterine and mammary tissues (Grese et al., *J. Med. Chem.* 1998; 41:1272–83). Furthermore, the incorporation of the nitrogen atom into a ring system such as in pyrrolidine or piperidine acts to prevent potential toxicity associated with N-dealkylation that has been shown for example to occur readily with the dimethylaminoethoxy side chain of tamoxifen (Gradishar and Jordan, *J. Clin. Oncol.* 1997; 15(2):840–52).

Certain preferred substituents for $R^2$ include but are not limited to $CH_2CH_2CH_3$, $CH_2C(CH_3)_2H$, $CH(OH)CH_2CH_3$, $CH=CHCH_3$, $CH=CHCH(CH_3)_2$, $CH_3C=CH_2$, $C=OCH_3$, $C=OCH_2CH_3$, $C=OCH(CH_3)_2$, $C=OCH=CH_2$, $C=OCH=C(CH_3)H$, $C=OCH=C(CH_3)_2$, $C(CH_3)=C(CH_3)_2$ and $CH(OH)CH_3$.

Certain preferred substituents for $R^3$ and $R^4$ include, but are not limited to hydrogen and hydrogen respectively, hydrogen and methyl respectively, methyl and hydrogen respectively or methyl and methyl respectively. It is believed that methylation at these sites will prevent the formation of potentially carcinogenic or mutagenic metabolites such as epoxides and will thus further reduce the potential toxicity of the structure.

Certain preferred substituents for $R^5$ include, but are not limited to OH or $OC=OCH_3$. The hydroxyl group at $R^5$ is preferred for hydrogen bond formation with the estrogen receptor and will eliminate the dependence on in vivo hydroxylation for biological activity. It is believed that compounds containing an ester or a methoxy substituent at the $R^5$ position would require metabolic activation for the functional group transformation to the hydroxyl form, which is required for high affinity interaction with the estrogen receptor.

In accordance with the present invention, there is therefore provided a compound of Formula 1 comprising A, B, C and D rings, or a pharmaceutically acceptable salt or ester thereof,

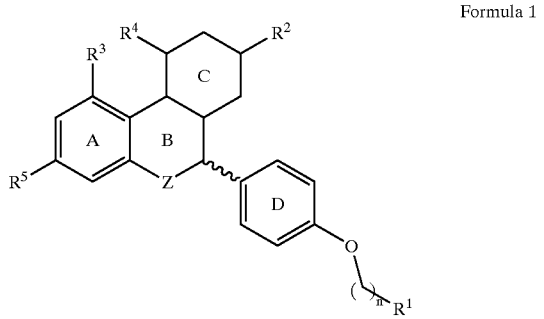

Formula 1 wherein $R^1$ represents a substituent selected from the group consisting of 1-pyrrolidinyl, 1-piperidinyl, methyl-1-pyrrolidinyl, dimethyl-1-pyrrolidino, 4-morpholino, dimethylamino, diisopropylamino and 1-hexamethyleneimino; wherein $R^2$ represents a substituent selected from the group consisting of $CH_2CH_2CH_3$, $CH_2C(CH_3)_2H$, $CH(OH)CH_2CH_3$, $CH=CHCH_3$, $CH=CHCH(CH_3)_2$, $CH_3C=CH_2$, $C=OCH_3$, $C=OCH_2CH_3$, $C=OCH(CH_3)_2$, $C=OCH=CH_2$, $C=OCH=C(CH_3)H$, $C=OCH=C(CH_3)_2$, $C(CH_3)=C(CH_3)_2$ and $CH(OH)CH_3$; wherein $R^3$ and $R^4$ can be a hydrogen atom or a methyl group; wherein $R^5$ is a hydroxy group or an ester group represented by the formula ($OC=OCH_3$); wherein "n" is an integer from 1 to 4; wherein "z" is a carbon atom, an oxygen atom or a sulfur atom; wherein at least one of the mentioned B-ring or C-ring is aromatic when "z" is a carbon atom and wherein the B-ring is not aromatic and the C-ring can be aromatic when "z" is either oxygen or sulfur.

In accordance with the present invention, there is also provided a process for the preparation of a compound of Formula 1, wherein "z" is an oxygen atom, involving the reaction of a molecule of Formula 1.8 comprising A, B, C and D rings;

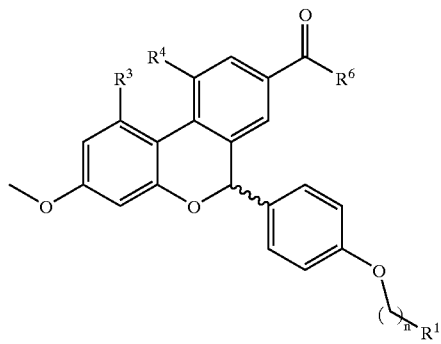

Formula 1-8 wherein $R^1$ represents a substituent selected from the group consisting of 1-pyrrolidinyl, 1-piperidinyl, methyl-1-pyrrolidinyl, dimethyl-1-pyrrolidino, 4-morpholino, dimethylamino, diisopropylamino and 1-hexamethyleneimino; wherein $R^6$ represents a substituent selected from the group consisting of $CH_3$, $CH_2CH_3$, $CH(CH_3)_2$, $CH=CH_2$, $CH=CHCH_3$ and $CH=C(CH_3)_2$; wherein $R^3$ and $R^4$ can be a hydrogen atom or a methyl group; wherein "n" is an integer from 1 to 4; and wherein the B-ring is non-aromatic and the C-ring is aromatic; with either $BBr_3$ or concentrated HBr followed by the recovery of the compound of FIG. 1 from the reaction mixture.

In accordance with the present invention, there is also provided a process for the preparation of a compound of Formula 1, wherein "z" is a carbon atom and wherein the B and C-rings are aromatic, involving the reaction of a molecule of Formula 2-7 comprising A, B, C and D rings;

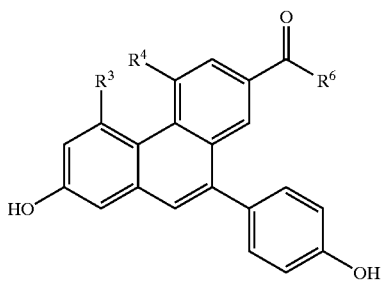

Formula 2-7 wherein $R^6$ represents a substituent selected from the group consisting of $CH_3$, $CH_2CH_3$, $CH(CH_3)_2$, $CH=CH_2$, $CH=CHCH_3$ and $CH=C(CH_3)_2$; wherein $R^3$ and $R^4$ can be a hydrogen or a methyl group; and wherein the mentioned B-ring and C-ring are aromatic; with a reagent having the general formula $Cl(CH_2)_nR^1$; wherein $R^1$ represents a substituent selected from the group consisting of 1-pyrrolidinyl, 1-piperidinyl, methyl-1-pyrrolidinyl, dimethyl-1-pyrrolidino, 4-morpholino, dimethylamino, diisopropylamino and 1-hexamethyleneimino and wherein "n" is an integer from 1 to 4; followed by the recovery of the compound of FIG. 1 from the reaction mixture.

In accordance with the present invention, there is also provided a process for the preparation of a compound of Formula 1, wherein "z" is a carbon atom, and wherein the B- and C-rings are aromatic, involving the reaction of a molecule of Formula 2-8 comprising A, B, C and D rings;

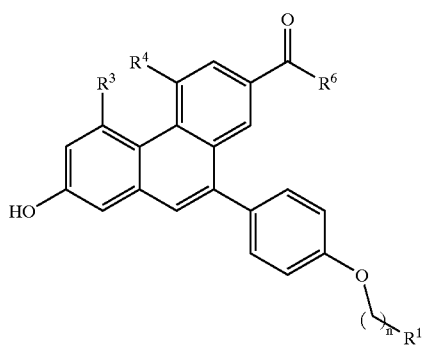

Formula 2-8

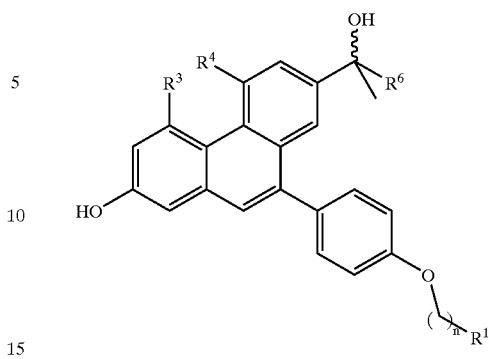

Formula 2.9 wherein $R^1$ represents a substituent selected from the group consisting of 1-pyrrolidinyl, 1-piperidinyl, methyl-1-pyrrolidinyl, dimethyl-1-pyrrolidino, 4-morpholino, dimethylamino, diisopropylamino and 1-hexamethyleneimino; wherein $R^6$ represents a substituent selected from the group consisting of $CH_3$, $CH_2CH_3$, $CH(CH_3)_2$, $CH=CH_2$, $CH=CHCH_3$ and $CH=C(CH_3)_2$; wherein $R^3$ and $R^4$ can be a hydrogen atom or a methyl group; wherein "n" is an integer from 1 to 4 and wherein the mentioned B-ring and C-ring are aromatic; with a reducing agent selected from the group consisting of $H_2$/Pd-C and $NaBH_4$ followed by the recovery of the compound of FIG. 1 from the reaction mixture.

In accordance with the present invention, there is also provided a process for the preparation of a compound of Formula 1, wherein "z" is a carbon atom, involving the reaction of a molecule of Formula 2-8 comprising A, B, C and D rings;

Formula 2-8

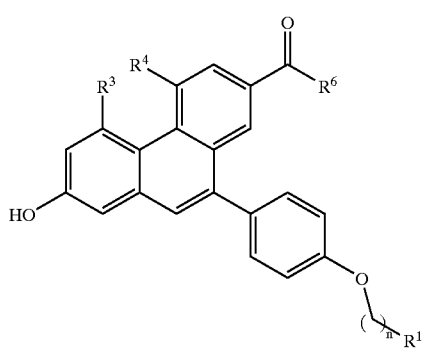

wherein $R^1$ represents a substituent selected from the group consisting of 1-pyrrolidinyl, 1-piperidinyl, methyl-1-pyrrolidinyl, dimethyl-1-pyrrolidino, 4-morpholino, dimethylamino, diisopropylamino and 1-hexamethyleneimino; wherein $R^6$ represents a substituent selected from the group consisting of $CH_3$, $CH_2CH_3$, $CH(CH_3)_2$, $CH=CH_2$, $CH=CHCH_3$ and $CH=C(CH_3)_2$; wherein $R^3$ and $R^4$ can be a hydrogen atom or a methyl group; wherein "n" is an integer from 1 to 4 and wherein the mentioned B-ring and C-ring are aromatic; with Li/NH₃ followed by the recovery of the compound of Formula 1 from the reaction mixture.

In accordance with the present invention, there is also provided a process for the preparation of a compound of Formula 1, wherein "z" is a carbon atom, involving the reaction of a molecule of Formula 2-9 comprising A, B, C and D rings;

wherein $R^1$ represents a substituent selected from the group consisting of 1-pyrrolidinyl, 1-piperidinyl, methyl-1-pyrrolidinyl, dimethyl-1pyrrolidino, 4-morpholino, dimethylamino, diisopropylamino and 1-hexamethyleneimino; wherein $R^6$ represents a substituent selected from the group consisting of $CH_3$, $CH_2CH_3$, $CH(CH_3)_2$, $CH=CH_2$, $CH=CHCH_3$ and $CH=C(CH_3)_2$; wherein $R^3$ and $R^4$ can be a hydrogen atom or a methyl group; wherein "n" is an integer from 1 to 4 and wherein the mentioned B-ring and C-ring are aromatic; with catalytic amount of sulfuric acid, resulting in a dehydration reaction, followed by the recovery of the compound of Formula 1 from the reaction mixture.

In accordance with the present invention there is provided a pharmaceutical composition comprising the compound represented by FIG. 1 and at least one pharmaceutically acceptable carrier.

In accordance with the present invention there is provided a process for the preparation of a non-steroidal estrogen receptor antaganist, involving the reaction of a molecule of Formula 1-8, as previously defined, with either $BBr_3$ or concentrated HBr followed by the recovery of the non-steroidal estrogen receptor antagonist from the reaction mixture.

In accordance with the present invention there is provided a process for the preparation of a non-steroidal estrogen receptor antaganist, involving the reaction of a molecule of Formula 2-7 with a with a reagent having the general formula $Cl(CH_2)_nR^1$; both as previously defined, followed by the recovery of the non steroidal estrogen anataganist antagonist from the reaction mixture.

In accordance with the present invention there is provided a process for the preparation of a non-steroidal estrogen receptor antaganist, involving the reaction of a molecule of Formula 2-8, as previously defined, with a with a reducing agent selected from the group consisting of $H_2$/Pd-C and $NaBH_4$, followed by the recovery of the non-steroidal estrogen receptor anataganist from the reaction mixture.

In accordance with the present invention there is provided a process for the preparation of a non-steroidal estrogen receptor antaganist, involving the reaction of a molecule of Formula 2-8, as previously defined, with with Li/NH₃, followed by the recovery of the non-steroidal estrogen receptor anataganist from the reaction mixture.

In accordance with the present invention there is provided a process for the preparation of a non-steroidal estrogen receptor antaganist, involving the reaction of a molecule of Formula 2-9, as previously defined, with a catalytic amount of sulfuric acid, resulting in a dehydration, followed by the recovery of the non-steroidal estrogen receptor antaganist from the reaction mixture.

Unless defined otherwise, the scientific and technological terms and nomenclature used herein have the same meaning as commonly understood by a person of ordinary skill. Generally, procedures such as recovering a-or more compounds from a reaction mixture are common methods used in the art. Such standard techniques can be found in reference manuals such as for example Gordon and Ford (The Chemist's Companion: A handbook of Practical Data, Techniques and References, John Wiley & Sons, New York, N.Y., 1972).

The present description refers to a number of routinely used chemical terms. Nevertheless, definitions of selected examples of such terms are provided for clarity and consistency.

As used herein, the terminology "pharmaceutical composition" or "pharmaceutical formulation", well known in the art, are used interchangeably.

As used herein, the terminology "recovering" a desired compound or the like, well known in the art, refers to such a desired compound having been isolated from other components of a reaction mixture.

As used herein, the terminology "concentrated", well known in the art, refers to an acidic solution having a concentration equal to or higher than 10%.

The present invention comprises the genus of compounds represented by formula I useful in the treatment and or prevention of a variety of disorders or conditions such as breast cancer, uterine cancer, ovarian cancer, bone tissue loss (osteoporosis), cardiovascular diseases, premenstrual syndrome, uterine fibroma, endometriosis, precocious puberty, vasomotor symptoms associated with menopause, atrophic vaginitis, CNS disorders (including Alzheimer's), infertility, glaucoma and elevated serum cholesterol.

It will be appreciated by those skilled in the art that reference herein to treatment extends to prophylaxis as well as the treatment of established diseases or symptoms. It will be further appreciated that the amount of a compound of the invention required for use in treatment will vary with the nature of the condition being treated, the age and condition of the patient and will be ultimately at the discretion of the attendant physician or medical practitioner. In general, however, doses employed for adult human treatment will typically be in the range of 0.001 mg/kg to about 100 mg/kg per day. The desired dose may conveniently be presented in a single dose or as divided doses administered at appropriate intervals, for example as two, three, four or more sub-doses per day.

The present invention also provides for novel pharmaceutical compositions of the compounds of Formula 1. While it is possible that compounds of the present invention may be therapeutically administered as the raw chemical, it is preferable to present the active ingredient as a pharmaceutical formulation. Accordingly, the present invention further provides for pharmaceutical formulations comprising a compound of Formula 1 or a pharmaceutically acceptable salt or ester thereof together with one or more pharmaceutically acceptable carriers and, optionally, other therapeutic and/or prophylactic ingredients. The carrier(s) must be "acceptable" in the sense of being compatible with the other ingredients of the formulation and not deleterious to the recipient thereof.

Formulations of the present invention may be administered in standard manner for the treatment of the indicated diseases, such as orally, parenterally, subligually, transdermally, rectally or via inhalation. For oral administration the composition may take the form of tablets or lozenges formulated in a conventional manner. For example, tablets and capsules for oral administration may contain conventional excipients such as binding agents, (for example, syrup, accacia, gelatin, sorbitol, tragacanth, mucilage of starch or polyvinylpyrrolidone), fillers (for example, lactose, sugar, microcrystalline cellulose, maize-starch, calcium phosphate or sorbitol), lubricants (for example, magnesium stearate, stearic acid, talc, polyethylene glycol or silica), disintegrants (for example, potato starch or sodium starch glycollate) or wetting agents, such as sodium lauryl sulphate. The tablets may be coated according to methods well-known in the art.

Alternatively, the compounds of the present invention may be incorporated into oral liquid preparations such as aqueous or oily suspensions, solutions, emulsions, syrups or elixirs. Moreover, formulations containing these compounds may be presented as a dry product for constitution with water or other suitable vehicle before use. Such liquid preparations may contain conventional additives such as suspending agents such as sorbitol syrup, methyl cellulose, glucose/sugar syrup, gelatin, hydroxyethylcellulose, carboxymethyl cellulose, aluminum stearate gel or hydrogenated edible fats; emulsifying agents such as lecithin, sorbitan mono-oleate or acacia; non-aqueous vehicles (which may include edible oils) such as almond oil, fractionated coconut oil, oily esters, propylene glycol or ethyl alcohol; and preservatives such as methyl or propyl p-hydroxybenzoates or sorbic acid.

Such preparations may also be formulated as suppositories, e.g., containing conventional suppository bases such as cocoa butter or other glycerides. Compositions for inhalation can be typically provided in the form of a solution, suspension or emulsion that may be administered as a dry powder or in the form of an aerosol using a conventional propellant such as dichlorodifluoromethane or trichlorofluoromethane. Typical transdermal formulations comprise a conventional aqueous or non-aqueous vehicle, such as creams, ointments, lotions or pastes or are in the form of a medicated plaster, patch or membrane.

Additionally, compositions of the present invention may be formulated for parental administration by injection or continuous infusion. Formulations for injection may take such forms as suspensions, solutions, or emulsions in oily or aqueous vehicles, and may contain formulatory agents such as suspending, stabilizing and/or dispersing agents. Alternatively, the active ingredient may be in powder form for constitution with a suitable vehicle (e.g., sterile, pyrogen-free water) before use.

Compositions of the present invention may be formulated for nasal administration. Such formulations may comprise the compound of the present invention and a non-toxic pharmaceutically acceptable nasal carrier. Suitable non-toxic pharmaceutically acceptable nasal carriers for use in the compositions of the present invention will be apparent to those skilled in the art of nasal pharmaceutical formulations. Obviously the choice of suitable carriers will depend on the exact nature of the particular nasal dosage form desired, as well as on the identity of the active ingredient(s). For example, whether the active ingredient(s) are to be formulated into a nasal solution (for use as drops or spray), a nasal suspension, a nasal ointment or a nasal gel. Preferred nasal dosage forms are solutions, suspensions and gels, which contain a major amount of water (preferably purified water) in addition to the active ingredient(s). Minor amounts of other ingredients such as pH adjusters (e.g., a base such as NaOH), emulsifiers or dispersing agents (e.g. polyoxyethylene 20 sorbitan mono-oleate), buffering agents, preservatives, wetting agents and jelling agents (e.g. methylcellulose) may also be present. Also, a sustained release composition (e.g. a sustained release gel) can be readily prepared.

The composition according to the invention may also be formulated as a depot preparation. Such long acting formulations may be administered by implantation (for example, subcutaneously or intramuscularly) or by intramuscular injection. Accordingly, the compounds of the invention may be formulated with suitable polymeric or hydrophobic materials (such as emulsion in an acceptable oil), ion exchange resins or as sparingly soluble derivatives or sparingly soluble salts.

BRIEF DESCRIPTION OF THE DRAWINGS

Having thus generally described the invention, reference will now be made to the accompanying drawings, showing by way of illustration a preferred embodiment thereof, and in which:

FIG. 1 shows the effects of the compound depicted by Formula 3 on the proliferation of MCF-7 estrogen-dependent cancer cells.

FIG. 2 shows the effects of the compound depicted by Formula 4 on the proliferation of MCF-7 estrogen-dependent cancer cells.

Other objects, advantages and features of the present invention will become more apparent upon reading the following non-restrictive description of preferred embodiments, with reference to the accompanying drawings, which are exemplary and should not be interpreted as limiting the scope of the present invention.

DESCRIPTION OF THE PREFERRED EMBODIMENT

The present invention relates to non-steroidal compounds that demonstrate high-binding affinity for the estrogen receptor, while being devoid of any agonistic effects on reproductive tissues and to non-steroidal compounds that have a high binding affinity for the estrogen receptor while also having some agonistic activity specific to the skeletal and cardiovascular systems.

In one preferred embodiment of the non-steroidal compounds, as described by Formula I, displaying high binding affinity for the estrogen receptor, the A, B, C and D rings are aromatic. $R^1$ is 1-piperidinyl, $R^2$ is C=OCH(CH$_3$)$_2$, $R^3$ is CH$_3$, $R^4$ is hydrogen, $R^5$ is hydroxyl and n=2. Preferably at least one embodiment is represented by the following Formula 3, or a pharmaceutically acceptable salt thereof:

Formula 3

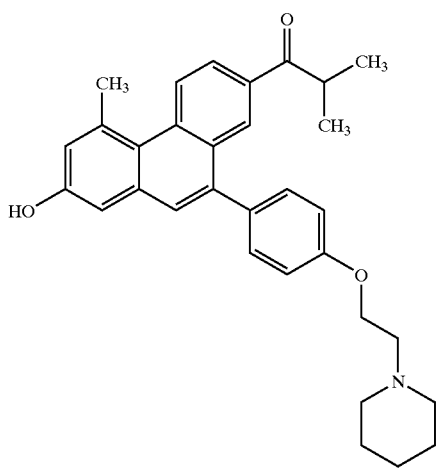

In another preferred embodiment of the invention, the A, B, C and D rings are aromatic. $R^1$ is 1-piperidinyl, $R^2$ is C=OCH$_3$, $R^3$ is CH$_3$, $R^4$ is hydrogen, $R^5$ is hydroxyl and n=2. Preferably at least one embodiment is represented by the following Formula 4, or a pharmaceutically acceptable salt thereof:

Formula 4

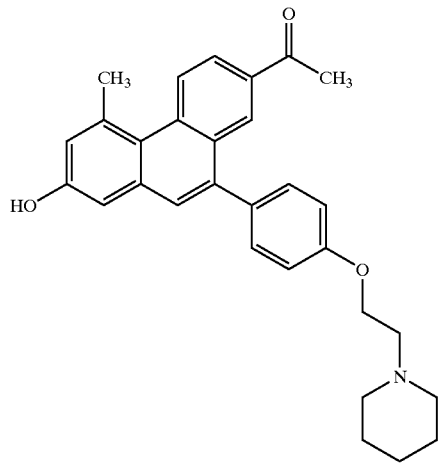

In another preferred embodiment of the invention, the A, B, C and D rings are aromatic. $R^1$ is 1-piperidinyl, $R^2$ is CH$_3$C=CH$_2$, $R^3$ is CH$_3$, $R^4$ is hydrogen, $R^5$ is hydroxyl and n=2. Preferably at least one embodiment is represented by the following Formula 5, or a pharmaceutically acceptable salt thereof:

Formula 5

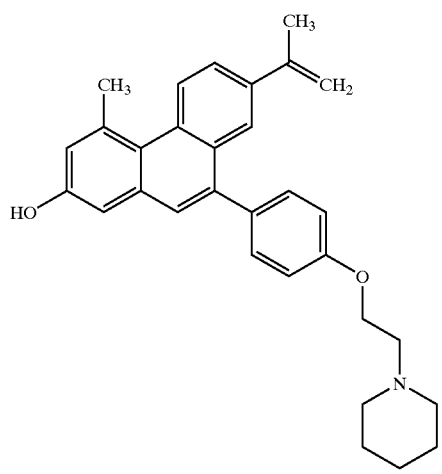

In another preferred embodiment of the invention, the A, B, C and D rings are aromatic. $R^1$ is 1-piperidinyl, $R^2$ is C(CH$_3$)=C(CH$_3$)$_2$, $R^3$ is CH$_3$, $R^4$ is hydrogen, $R^5$ is hydroxyl and n=2. Preferably at least one embodiment isrepresented by the following Formula 6, or a pharmaceutically acceptable salt thereof:

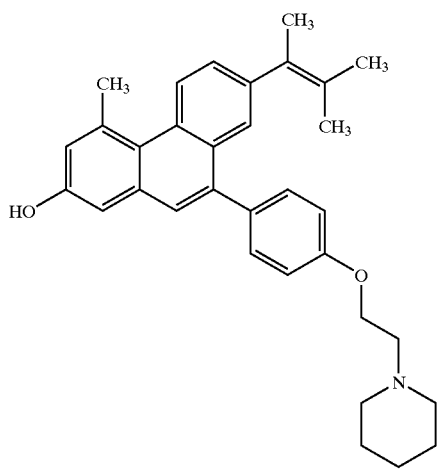

Formula 6

In yet another preferred embodiment of the invention, the A, B, C and D rings are aromatic. $R^1$ is 1-piperidinyl, $R^2$ is $CH(OH)CH_3$, $R^3$ is $CH_3$, $R^4$ is hydrogen, $R^5$ is hydroxyl and n=2. Preferably at least one embodiment is represented by the following Formula 7, or a pharmaceutically acceptable salt thereof:

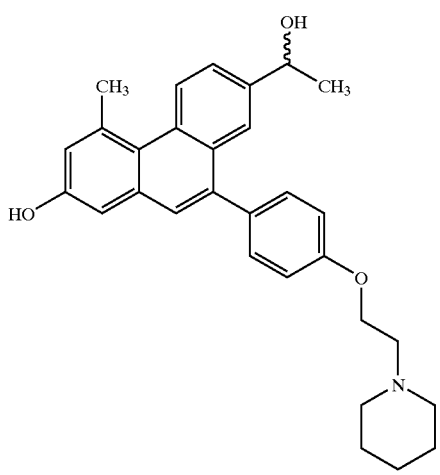

Formula 7

Synthesis

Set forth below is a preferred synthesis scheme for the preparation of certain preferred embodiments of the anti-estrogens in accordance with the invention. The synthetic steps set forth below are set forth merely by way of examples. Those skilled in the art will readily recognize alternative synthetic pathways and variations capable of producing a variety of anti-estrogens in accordance with the present invention.

Compounds of Formula 1 where Z=O and the B ring is non-aromatic are prepared as depicted in Scheme 1. Compounds 1-1 are made by acylation of substituted methyl 5-acetyl salicylates using trifluoromethanesulfonic anhydride. Dimethoxyphenylboronic acids dissolved in a polar protic organic solvent, ethanol for example, are added to a solution of 1-1 dissolved in an organic solvent, 1,2-dimethoxyethane for example. To this mixture an inorganic base, such as potassium carbonate, and a catalytic amount of tetrakis(triphenylphosphine)palladium were added and the mixture refluxed to give the ester biphenyls 1-2 (Suzuki Coupling). Alkylation of 1-2 using a strong base, lithium diisopropylamide (LDA) for example, and an alkyl halide gives further alkylated biphenyls 1-3. The saponification of 1-3 in aqueous base, such as potassium hydroxide, at reflux, affords the free acid biphenyls 1-4. Cyclization to the dibenzo lactones 1-5 occurs by treatment of 1-4 with thionyl chloride followed by aluminum trichloride in a refluxing organic solvent such as 1,2-dichloroethane. Treatment of 1-5 with a diol, ethylene glycol, for example, in the presence of a catalytic amount of an acid such as p-toluenesulfonic acid in a refluxing organic solvent affords the ketone protected dibenzo[c]chromen-6-ones 1-6. Transmetallation of 4-[2-(1-amino)-alkoxy]-bromobenzenes using n-butyl lithium or magnesium metal yields the corresponding lithium or magnesium reagents which were subsequently reacted with 1-6 to afford the protected dibenzopyran hemiketals 1-7. Treatment of 1-7 with triethylsilane, followed by either boron trifluoride-etherate or trifluoroacetic acid, reduces the hemiketal with concomitant deprotection of the ketone, to give the substituted dibenzopyran ethers 1-8. Treatment of 1-8 with either boron tribromide or concentrated hydrogen bromide (48%) yields compounds of Formula 1 (depicted by structure 1-9), more specifically compounds of Formula 1 wherein Z=O, the B-ring is non-aromatic, wherein $R^2$ is represented by $C=OR^6$ and wherein $R^6$ is as previously defined. It is readily recognized by those skilled in the art that compounds of general structure 1-9 can be further reacted with a variety of Grignard reagents, followed by heating in a non-aqueous acidic medium such as glacial acetic acid containing sulfuric acid, giving rise to the corresponding alkene products. It is also readily recognized by those skilled in the art that compounds of general structure 1-9 can be further reacted with a reducing agent such as hydrogen gas over palladized charcoal or with a hydride reducing agent such as $NaBH_4$, giving rise to the corresponding alcohols. It is readily recognized that these alcohols can be reacted in a non-aqueous medium such as glacial acetic acid containing sulfuric acid, to yield the corresponding alkene products.

Scheme 1

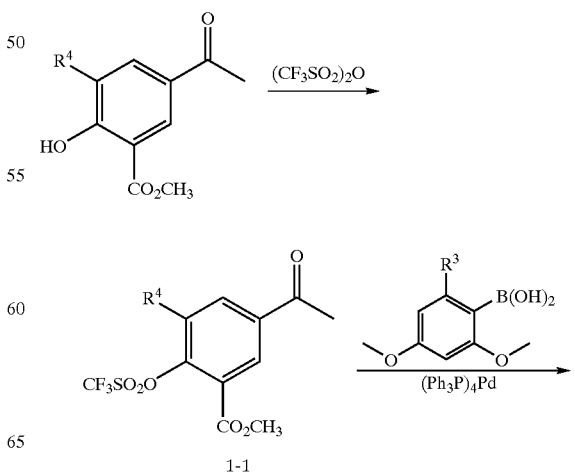

1-1

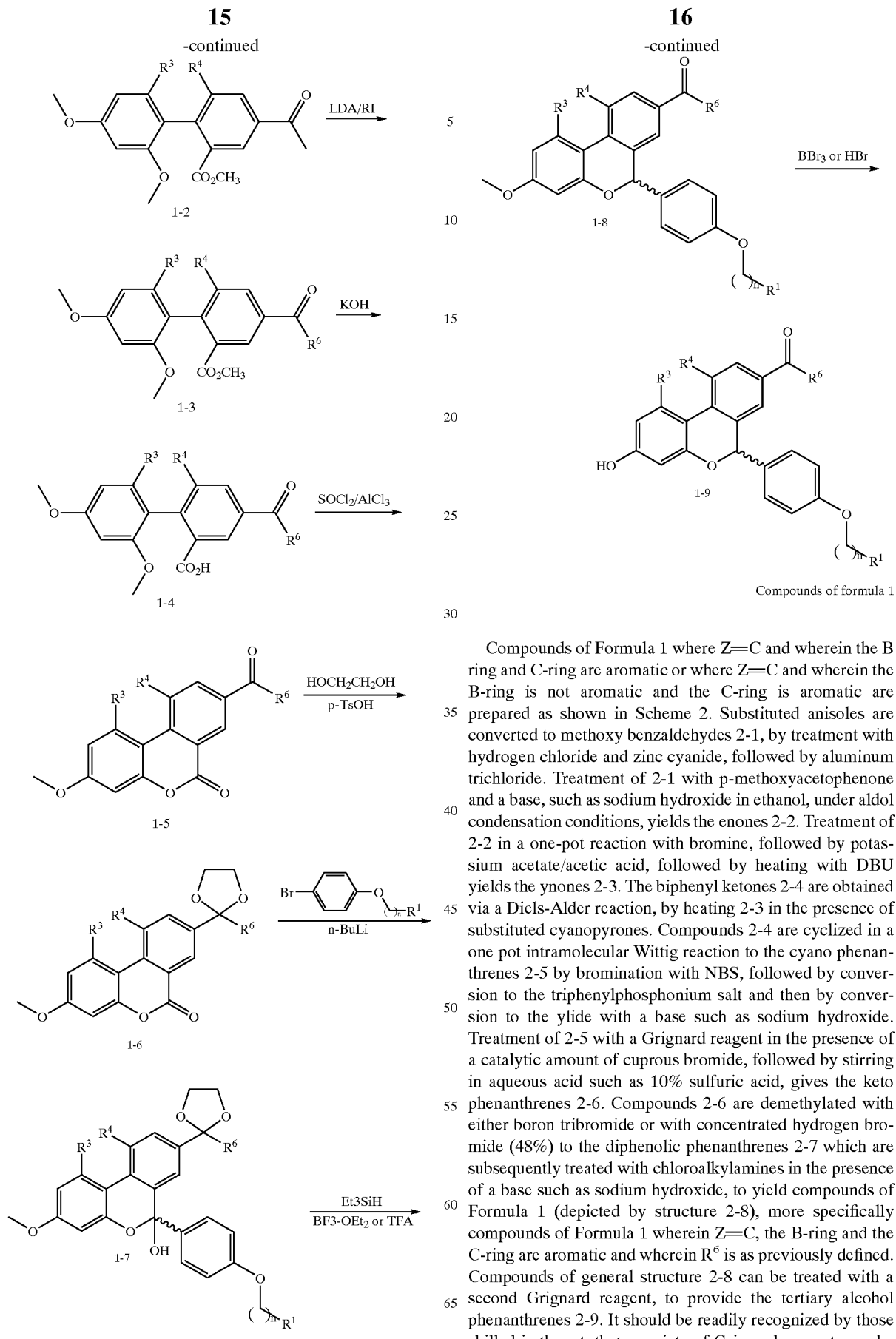

Compounds of Formula 1 where Z=C and wherein the B ring and C-ring are aromatic or where Z=C and wherein the B-ring is not aromatic and the C-ring is aromatic are prepared as shown in Scheme 2. Substituted anisoles are converted to methoxy benzaldehydes 2-1, by treatment with hydrogen chloride and zinc cyanide, followed by aluminum trichloride. Treatment of 2-1 with p-methoxyacetophenone and a base, such as sodium hydroxide in ethanol, under aldol condensation conditions, yields the enones 2-2. Treatment of 2-2 in a one-pot reaction with bromine, followed by potassium acetate/acetic acid, followed by heating with DBU yields the ynones 2-3. The biphenyl ketones 2-4 are obtained via a Diels-Alder reaction, by heating 2-3 in the presence of substituted cyanopyrones. Compounds 2-4 are cyclized in a one pot intramolecular Wittig reaction to the cyano phenanthrenes 2-5 by bromination with NBS, followed by conversion to the triphenylphosphonium salt and then by conversion to the ylide with a base such as sodium hydroxide. Treatment of 2-5 with a Grignard reagent in the presence of a catalytic amount of cuprous bromide, followed by stirring in aqueous acid such as 10% sulfuric acid, gives the keto phenanthrenes 2-6. Compounds 2-6 are demethylated with either boron tribromide or with concentrated hydrogen bromide (48%) to the diphenolic phenanthrenes 2-7 which are subsequently treated with chloroalkylamines in the presence of a base such as sodium hydroxide, to yield compounds of Formula 1 (depicted by structure 2-8), more specifically compounds of Formula 1 wherein Z=C, the B-ring and the C-ring are aromatic and wherein $R^6$ is as previously defined. Compounds of general structure 2-8 can be treated with a second Grignard reagent, to provide the tertiary alcohol phenanthrenes 2-9. It should be readily recognized by those skilled in the art, that a variety of Grignard reagents can be employed in the formation of the tertiary alcohol phenanthrenes 2-9. It should also be readily recognized that the tertiary alcohol phenanthrenes 2-9 can be further reacted by stirring in acetic acid at elevated temperatures, preferably 75° C., to yield the corresponding alkene products. Compounds of general structure 2-8 can be converted to the corresponding alcohols 2-10, via hydrogenation using hydrogen gas over palladized charcoal. The corresponding alcohols 2-10 can also be obtained by using a "hydride reducing agent such as sodium borohydride. Alternatively, compounds of general structure 2-8 can also be reduced via "dissolved metal reduction" by using for example, Li/NH$_3$ providing compounds of general structure 2-12. It is readily recognized by those skilled in the art that the carbonyl functionality of compounds of general structure 2-8 can be protected prior to reaction with Li/NH$_3$ and then deprotected, in order to maintain the carbonyl functionality providing compounds of general structure 2-11. It is also readily recognized that compounds of general structure 2-11 can be further reacted with a variety of Grignard reagents, followed by heating in a non-aqueous acidic medium such as glacial acetic acid containing sulfuric acid, giving rise to the corresponding alkene products. It is also readily recognized that compounds of general structure 2-11 can be further reacted with a reducing agent such as hydrogen gas over palladized charcoal or with a hydride reducing agent such as NaBH$_4$, giving rise to the corresponding alcohols. It should also be readily recognized that these alcohols can be reacted in a non-aqueous medium such as glacial acetic acid containing sulfuric acid, to yield the corresponding alkene products.

Scheme 2

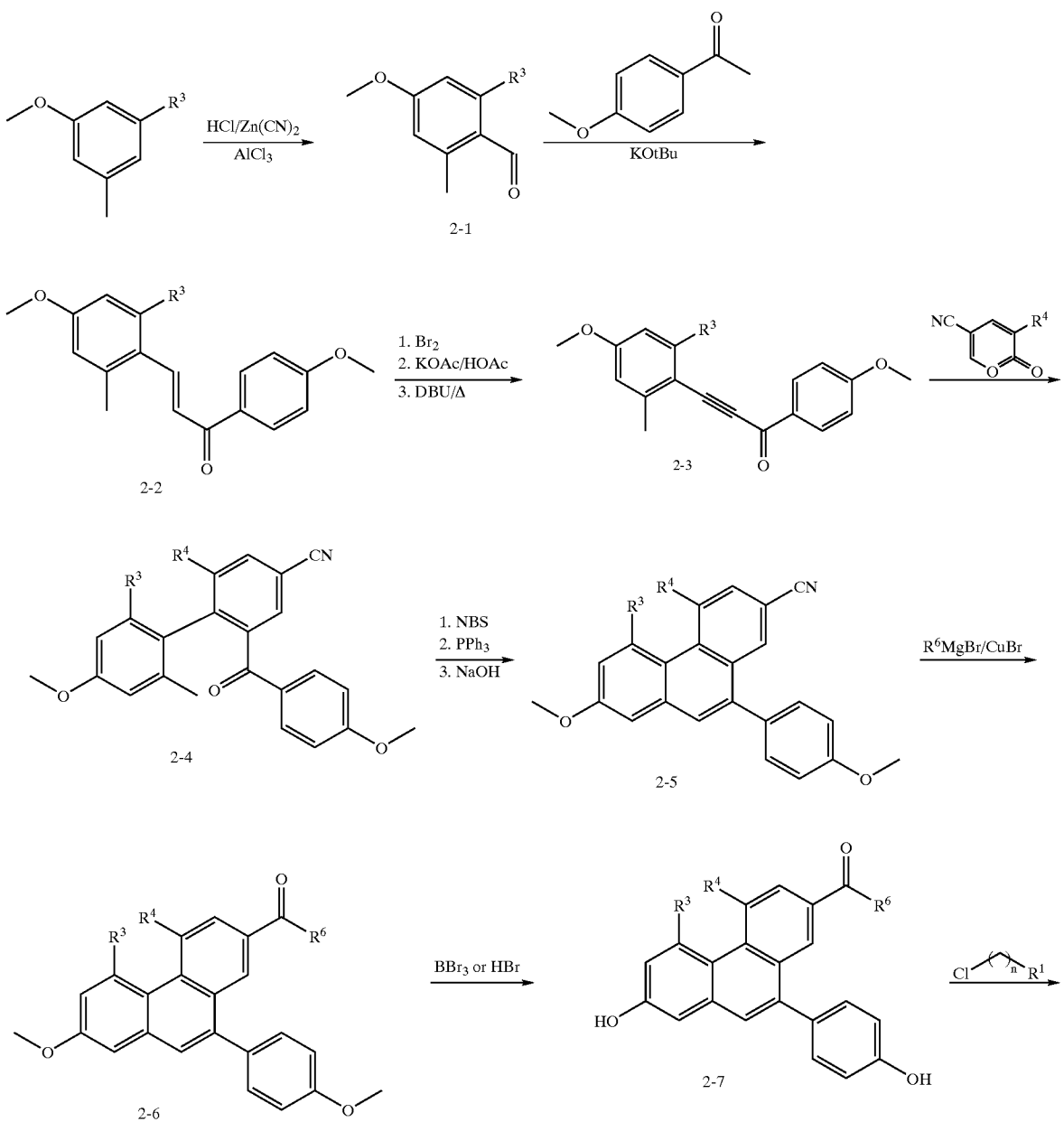

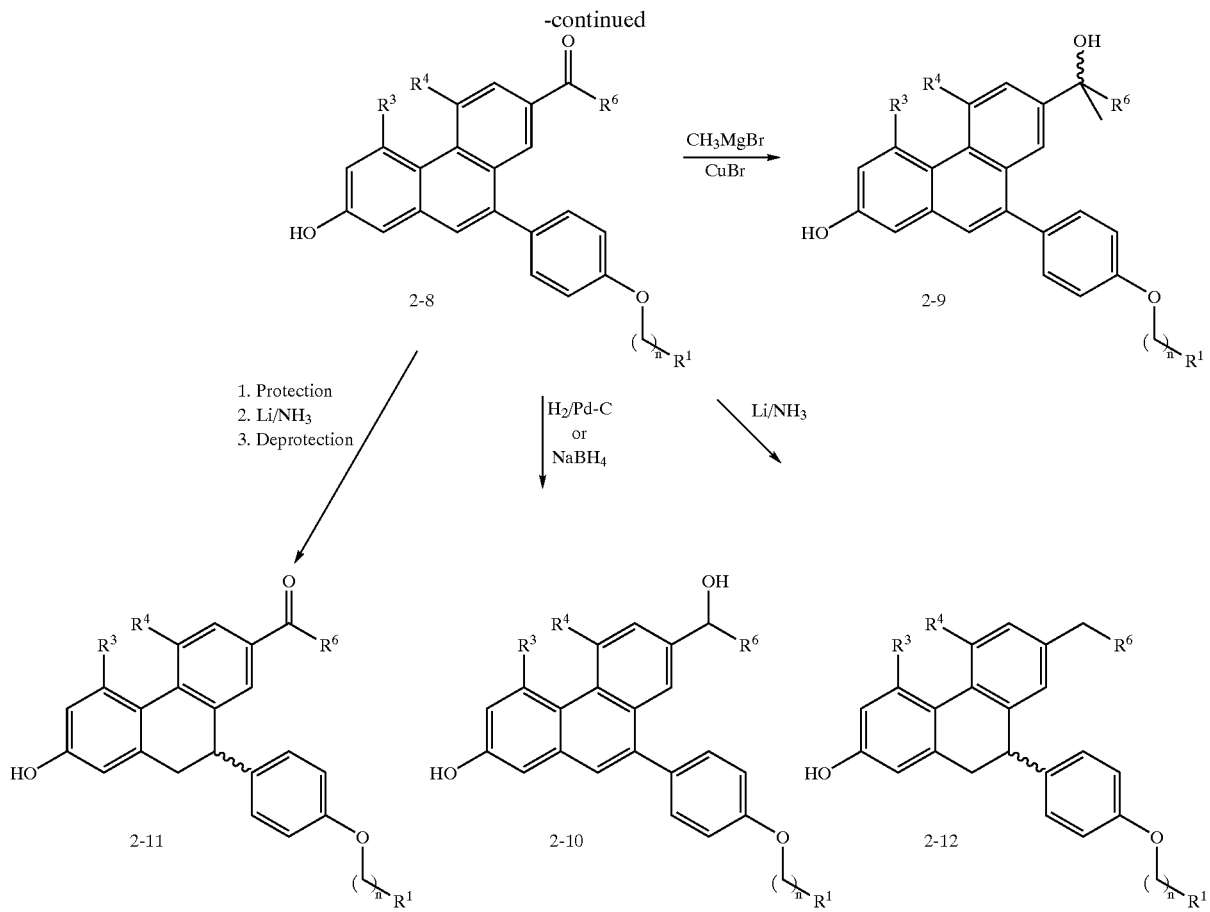

The present invention is illustrated in further detail by the following non-limiting examples.

EXAMPLE 1

ND-77

Synthesis of (+)-1-[3-hydroxy-6-[4-(2-piperidin-1-yl-ethoxy)-phenyl]-6H-benzo[c]chromen-8-yl]-1-ethanone Step A: 5-acetyl-2-(trifluoro-methyl-sulfonyloxy)-benzoic Acid, Methyl Ester Methyl 5-acetylsalicylate (25.0 g, 129 mmol) was mixed with $CH_2Cl_2$ (250 ml) and pyridine (60 ml) under argon at 0° C. Trifluormethanesulfonic anhydride (37.9 g, 133 mmol) was added over 20 min. The reaction was stirred for an additional 30 min and then quenched with water (500 ml). The organic layer was separated and washed three times with 5% HCl (80 ml). After removing the solvent, the solid obtained was dried under vacuum to yield 40.3 g (96%) of the title compound. $^1$H-NMR (400 MHz, $CDCl_3$) $\delta_H$ 2.56 (3H, s, $COCH_3$), 3.89 (3H, s, $OCH_3$), 7.32 (1H, d, ArH), 8.12 (1H, d, ArH), 8.52 (1H, s, ArH).

Step B: 4-acetyl-2',4'-dimethoxy-biphenyl-2-carboxylic Acid, Methyl Ester 2,4-Dimethoxyphenylboronic acid (24.0 g, 134 mmol) was dissolved in ethanol (250 ml). The compound from Step A (21 g, 67 mmol) was dissolved in 1,2-dimethoxyethane (375 ml). The two solutions were mixed with tetrakis(triphenylphosphine)palladium (1 g, 0.9 mmol) and $K_2CO_3$ (8.9 g, 64 mmol). The resulting suspension was refluxed for 2 h and then poured into saturated $NaHCO_3$ (1 L). The mixture was extracted three times with $CH_2Cl_2$ (400 ml) and dried over $Na_2SO_4$. The solvent was removed to yield 35.6 g of crude product which was chromatographed on silica gel with hexane/ethyl acetate (2:1) followed by hexane/ethyl acetate (1:1) to yield 18.3 g (87%) of the title compound. $^1$H-NMR (400 MHz, $CDCl_3$) $\delta_H$ 2.68 (3H, s, $COCH_3$), 3.73 (3H, s, $OCH_3$), 3.76 (3H, s, $OCH_3$), 3.88 (3H, s, $CO_2CH_3$), 6.52 (1H, s ArH), 6.62 (1H, d, ArH), 7.23 (1H, d, ArH), 7.45 (1H, d, ArH), 8.13 (1H, d, ArH), 8.42 (1H, s, ArH).

Optionally, this compound can be dissolved in DME under argon and cooled to −20° C. and reacted with LDA and the resulting enolate trapped with an appropriate alkyl halide such as for example methyl iodide.

Step C: 4-acetyl-2',4'-dimethoxy-biphenyl-2-carboxylic acid

The compound from Step B (9.3 g, 29.6 mmol) was mixed with distilled water (500 ml) and KOH (3.3 g, 59 mmol) added. The mixture was refluxed for 3 h and then acidified to pH 1 with concentrated HCl. The resulting precipitate was filtered and dried under vacuum at 45° C. for 3 h to yield 8.1 g (90%) of the title compound. $^1$H-NMR (400 MHz, $CDCl_3$) $\delta_H$ 2.71 (3H, s, $COCH_3$), 3.92 (3H, s, $OCH_3$), 3.96 (3H, s, $OCH_3$), 6.94 (1H, d, ArH), 6.96 (1H, s, ArH), 7.55 (1H, d, ArH), 8.17 (1H, d, ArH), 8.51 (1H, s, ArH).

Step D: 8-acetyl-3-methoxy-benzo[c]chromen-6-one

The compound from Step C was mixed with 1,2-dichloroethane (60 ml) and $SOCl_2$ (1.7 ml, 23 mmol) was added. The mixture was refluxed for 90 min and then cooled to 0° C. $AlCl_3$ (2.3 g, 17.3 mmol) was added and the reaction stirred at room temperature overnight. The solvent was removed and the crude product chromatographed on silica gel with hexane/ethyl acetate (1:1) to yield 5.1 g (90%) of the title compound. $^1$H-NMR (400 MHz, CDCl$_3$) δ$_H$ 2.74 (3H, s, COCH$_3$), 3.94 (3H, s, OCH$_3$), 6.92 (1H, s, ArH), 6.99 (1H, d, ArH), 8.02 (1H, d, ArH), 8.11 (1H, d, ArH), 8.41 (1H, d, ArH), 8.91 (1H, s, ArH).

Step E: 3-methoxy-8-(2-methyl-[1,3]-dioxolan-2-yl)-benzo[c]chromen-6-one

The compound from Step D (5.2 g, 19 mmol), ethylene glycol (4.4 g, 71 mmol) and a catalytic amount of p-toluenesulfonic acid (0.2 g) were dissolved in benzene (300 ml) and refluxed for 28 h. The solvent was removed and the crude product chromatographed on silica gel with hexane/ethyl acetate (2:1) to yield 3.6 g (60%) of the title compound. $^1$H-NMR (400 MHz, CDCl$_3$) δ$_H$ 1.75 (3H, s, CH$_3$), 3.82 (2H, t, OCH$_2$), 3.91 (3H, s, OCH$_3$), 4.10 (2H, t, OCH$_2$), 6.93 (1H, s, ArH), 6.98 (1H, d, ArH), 7.47 (3H, m, ArH), 8.04 (1H, s, ArH).

Step F: 1-[2-(4-bromo-phenoxy)-ethyl]-piperidine 4-bromophenol (5.2 g, 30 mmol), K$_2$CO$_3$ (10.4 g, 75 mmol) and anhydrous DMF (50 ml) were mixed together under Ar and heated at 100° C. 1-(2-chloroethyl)-piperidine hydrochloride (5.5 g, 30 mmol) was added in portions over 10 min and the reaction maintained at 100° C. for 1.5 h. After cooling the reaction, the solid was filtered off and the solvent removed under vacuum. The crude product was chromatographed on silica gel with methanol/ethyl acetate (3:1) to yield 6.7 g (78%) of the title compound. $^1$H-NMR (400 MHz, CDCl$_3$) δ$_H$ 1.44 (2H, m, NCH$_2$CH$_2$C$\underline{H}_2$), 1.59, (4H, m, NCH$_2$C$\underline{H}_2$), 2.48 (4H, m, NC$\underline{H}_2$CH$_2$), 2.73 (2H, t, NC$\underline{H}_2$CH$_2$O), 4.03 (2H, t, NCH$_2$C$\underline{H}_2$O), 6.76 (2H, d, ArH), 7.33 (2H, d, ArH).

Step G: (+)-3-methoxy-8-(2-methyl)-[1,3]-dioxolan-2-yl)-6-[4-(2-piperidin-1-yl-ethoxy)-phenyl]-6H-benzo[c]chromen-6ol 1-[2-(4-bromo-phenoxy)-ethyl]-piperidine (0.76 g, 2.7 mmol) from Step F was dissolved in THF (15 ml) under Ar and cooled to −78° C. n-Butyl lithium (10.0 M, 0.26 ml, 2.6 mmol) was added and the mixture was stirred at −78° C. for 1 hour. The compound from Step E (1.11 g, 3.56 mmol) was dissolved in THF (35 ml) under Ar and cooled to −78° C. to which the freshly prepared lithium salt of 1-(2-(4-bromophenoxy)-ethyl)-piperidine was transferred via a cannula. The reaction was stirred for 2 h. Water (150 ml) was added and the reaction extracted three times with ethyl acetate (150 ml). After removing the solvent the crude product was chromatographed on silica gel with 7% CH$_3$OH/CH$_2$Cl$_2$ to yield 0.56 g (48%) of the title compound. $^1$H-NMR (400 MHz, CDCl$_3$) δ$_H$ 1.44 (2H, m, NCH$_2$CH$_2$C$\underline{H}_2$), 1.59 (4H, m, NCH$_2$C$\underline{H}_2$CH$_2$) 1.61 (3H, s, CH$_3$), 2.25 (4H, m, NC$\underline{H}_2$CH$_2$CH$_2$), 2.83 (2H, m, NC$\underline{H}_2$CH$_2$O), 3.78 (2H, m, OC$\underline{H}_2$), 3.85 (3H, s, OCH$_3$), 4.01 (2H, m, OCH$_2$), 4.18 (2H, m, NCH$_2$C$\underline{H}_2$O), 6.69 (1H, s, ArH), 6.73 (1H, d, ArH), 6.96 (2H, d, ArH), 7.17 (1H, s, ArH), 7.56 (1H, m, ArH), 7.60 (2H, d, ArH), 7.76 (2H, m, ArH).

Step H: (+)-1-[3-methoxy-6-[4-(2-piperidin-1-yl-ethoxy)-phenyl]-6H-benzo[c]chromen-8-yl]-ethanone The compound from Step G (1.66 g, 3.2 mmol) was dissolved in CH$_2$Cl$_2$ (90 mL) and cooled to −78° C. Et$_3$SiH (3.1 ml, 19.2 mmol) and BF$_3$-Et$_2$O (2.6 ml, 19.2 mmol) were added slowly under Ar. The mixture was stirred at −78° C., then at room temperature overnight. Saturated NaHCO$_3$ (100 ml) was added and the mixture extracted three times with ethyl acetate (150 ml). The combined organic layer was washed with brine (100 ml) and dried over MgSO$_4$. The solvent was removed and the crude product was chromatographed on silica gel with 7% CH$_3$OH/CH$_2$Cl$_2$ to yield a fraction containing a mixture of the title compound along with side products and a fraction containing 0.52 g (32%) of the title compound. $^1$H-NMR (400 MHz, CDCl$_3$) δ$_H$ 1.42 (2H, m, NCH$_2$CH$_2$C$\underline{H}_2$), 1.59 (4H, m, NCH$_2$C$\underline{H}_2$CH$_2$), 2.50 (7H, m, NC$\underline{H}_2$CH$_2$CH$_2$ and COCH$_3$), 2.76 (2H, m, NC$\underline{H}_2$CH$_2$O), 3.77 (3H, s, OCH$_3$), 4.08 (2H, m, NCH$_2$C$\underline{H}_2$O), 6.14 (1H, s, Ph$_2$C$\underline{H}$O), 6.50 (1H, s, ArH), 6.61 (1H, d, ArH), 6.86 (2H, d, ArH), 7.22 (2H, d, ArH), 7.45 (1H, s, ArH), 7.66 (1H, d, ArH), 7.72 (1H, d, ArH), 7.93 (1H, d, ArH).

Step I: (+)-1-[3-hydroxy-6-[4-(2-piperidin-1-yl-ethoxy)phenyl]-6H-benzo[c]chromen-8-yl]-ethanone The mixture containing the compound from Step H (0.25 g, 0.565 mmol) was dissolved in CH$_2$Cl$_2$ (40 ml) and cooled to −78° C. and BBr$_3$ in CH$_2$Cl$_2$ (1M, 11 ml) was added. The mixture was kept at −78° C. and allowed to warm to 15° C. overnight. The reaction was quenched with saturated NaHCO$_3$ (5 ml) and extracted with CH$_2$Cl$_2$ (20 ml). The organic layer was washed with saturated NaHCO$_3$, water and dried over Na$_2$SO$_4$. The solvent was removed and the crude product purified by preparative TLC plates. $^1$H-NMR (400 MHz, CDCl$_3$) δ$_H$ 1.55 (2H, m, NCH$_2$CH$_2$C$\underline{H}_2$), 1.80 (4H, m, NCH$_2$C$\underline{H}_2$CH$_2$), 2.56 (3H, s, COCH$_3$), 2.81 (4H, m, NC$\underline{H}_2$CH$_2$CH$_2$), 3.01 (2H, m, NC$\underline{H}_2$CH$_2$O), 4.22 (2H, m, NCH$_2$C$\underline{H}_2$O), 6.13 (1H, s, Ph$_2$C$\underline{H}$O), 6.50 (1H, s, ArH), 6.60 (1H, d, ArH), 6.80 (2H, d, ArH), 7.21 (2H, d, ArH), 7.49 (1H, s, ArH), 7.65 (1H, d, ArH), 7.74 (1H, d, ArH), 7.97 (1H, d, ArH).

EXAMPLE 2

ND73

Synthesis of 1-[7-hydroxy-5-methyl-10-[4-(2-piperidin-1-yl-ethoxy)-phenyl]-phenanthren-2-yl]-2-methyl-propan-1-one Step A: 4-methoxy-2,6-dimethyl-benzaldehyde 3,5-Dimethylanisole (25.3 g, 0.186 mol) was added to (CHCl$_2$)$_2$ (180 ml) and maintained at 17° C. Zn(CN)$_2$ (37.1 g, 0.316 mol) was added and HCl gas was bubbled through the mixture with stirring. The rate of HCl gas addition was adjusted to allow for HCl absorption. After 1 hour of HCl gas addition the rate of absorption significantly decreased and AlCl$_3$ (37.2 g, 0.279 mol) was added. A slow rate of HCl gas flow was maintained. The temperature was increased to 55° C. and the reaction maintained at this temperature for 3 h. The reaction mixture was then poured onto a mixture of ice (800 ml) and concentrated HCl (800 ml). The content of the reaction vessel was then rinsed twice with CHCl$_3$ (200 ml) and added to the aqueous layer. The resulting biphasic system was stirred at 60–65° C. overnight. The organic layer was separated and the aqueous layer washed with 200 ml and 150 ml of CHCl$_3$. The combined extract washed with deionized water (3×200 ml) and the organic solvents removed by evaporation. The concentrate was transferred to a distillation flask equipped with a Vigreux column and distilled at 110° C. (0.7 mm Hg) to give a distillate (29.2 g) containing residual (CHCl$_2$)$_2$ and a mixture composed of the desired 4-methoxy-2,6-dimethylbenzaldehyde isomer and some of the unwanted 6-methoxy-2,4-dimethylbenzaldehyde isomer in a 2:1 ratio. The distillate was added to methyl t-butyl ether and crystallized overnight at 4° C. The crystals were filtered and washed with 5 ml of a mixture of ethyl acetate:hexane (1:12) to give 7.84 g of the title compound. The mother liquor was concentrated and chromatographed on silica gel with ethyl acetate/hexane (1:12) to give an additional 10.74 g of the title compound (18.58 g total, 61%). $^1$H-NMR (400 MHz, CDCl$_3$) δ$_H$ 2.62 (6H, s, CH$_3$), 6.59 (2H, s, ArH), 10.48 (1H, s, CHO).

Step B: 3-(4-methoxy-2,6-dimethyl-phenyl)-1-(4-methoxyphenyl)-propenone

The compound from Step A (18.58 g, 0.113 mol) and 4-methoxyacetophenone (17.42 g, 0.116 mol) were added to anhydrous ethanol (110 ml) and NaOH (2.5 g) and stirred overnight at room temperature. The precipitate that formed was filtered, washed with water (3×50 ml) and dried overnight under high vacuum to give 29.8 g of the title compound. The filtrate was stirred overnight to give and additional 1.1 g (total 30.9 g, 92%). $^1$H-NMR (400 MHz, CDCl$_3$) δ2.44 (6H, s, CH$_3$), 3.83 (3H, s, OCH$_3$), 3.90 (3H, s, OCH$_3$), 6.66 (2H, s, ArH), 6.99 (2H, d, ArH), 7.16, (1H, d, ArCH), 7.96 (1H, d, COCH), 8.01 (2H, d, ArH).

Step C: 3-(4-methoxy-2,6-dimethyl-phenyl)-1-(4-methoxyphenyl)-propynone i. 2,3-dibromo-3-(4-methoxy-2,6-dimethylphenyl)-1-(4-methoxyphenyl)-propan-1-one.

To a solution of the compound from Step B (30.9 g, 0.104 mol), dissolved in CH$_2$Cl$_2$ (200 ml) and cooled in an ice bath, was added a solution of Br$_2$ (16.7 g, 5.37 ml, 0.104 mol) in CH$_2$Cl$_2$ (100 ml) over 105 min. with additional stirring for 2 h. A second portion of Br$_2$ (1.2 ml) in CH$_2$Cl$_2$ (50 ml) was added over 30 min and the reaction left at room temperature overnight, followed by the evaporation of the solvent to give the title compound that was used without further purification. $^1$H-NMR (400 MHz, CDCl$_3$) δ$_H$ 2.51 (3H, s, CH$_3$), 2.71 (3H, s, CH$_3$), 3.81 (3H, s, OCH$_3$), 3.92 (3H, s, OCH$_3$), 6.16 (1H, d, COCHBr), 6.24 (1H, d, ArH), 6.34 (1H, d, ArCHBr), 6.66 (1H, d, ArH), 7.03 (2H, d, ArH), 8.07 (2H, d, ArH).

ii. 2-bromo-1-(4-methoxy-2,6-dimethylphenyl)-3-(4-methoxyphenyl)-3-oxo-propyl ester.

The crude compound from step i was added to acetic acid (550 mL) and KOAc (12.5 g, 0.13 mol) and stirred for 6 hours. Additional KOAc (3.0 g) was added and the mixture stirred overnight. The HOAc was evaporated and the residue dissolved in water (300 ml), extracted with CHCl$_3$ (300 ml), the CHCl$_3$ extract washed with water (3×150 ml) and concentrated to give the title compound that was used without further purification. $^1$H-NMR (400 MHz, CDCl$_3$) δ$_H$ 1.88 (3H, s, COCH$_3$), 2.58 (3H, s, CH$_3$), 2.65 (3H, s, CH$_3$), 3.80 (3H, s, OCH$_3$), 3.91 (3H, s, OCH$_3$), 5.76 (1H, d, COCHBr), 6.60 (2H, s, ArH), 6.87 (1H, d, ArCHO), 6.66 (1H, d, ArH), 7.02 (2H, d, ArH), 8.04 (2H, d, ArH).

iii. 3-(4-methoxy-2,6-dimethylphenyl)-1-(4-methoxyphenyl)-2-propynone.

DBU (36.2 g, 0.238 mol) and the crude compound from step ii were added to THF (350 ml) and heated to 55° C. overnight. The reaction mixture was filtered and the precipitate washed with THF (2×100 ml). The filtrate was evaporated and the residue dissolved in CHCl$_3$ (300 ml), washed with water (2×150 ml), 8% HCl (pH 2,150 mL), and water (2×150 ml). It was noted that the final separation was made easier if an aqueous solution of NaHCO$_3$ (15 ml) was added to the last extraction. After evaporation of the solvent and drying overnight under high vacuum, the crude material was crystallized from anhydrous toluene (30 ml) by cooling to room temperature and then to 4° C. to give 22.4 g, (73%) of the title compound. $^1$H-NMR (400 MHz, CDCl$_3$) δ$_H$ 2.55 (6H, s, CH$_3$), 3.82 (3H, s, OCH$_3$), 3.89 (3H, s, OCH$_3$), 6.65-8.22 (6H, ArH).

Step D: 4'-methoxy-2',6'-dimethyl-2-(4-methoxybenzoyl)-biphenyl-4-carbonitrile

The compound from Step C, iii (4.20 g, 15.7 mmol) and 5-cyanopyrone (1.90 g, 15.7 mmol) (Helv. Chim. Acta (1990) 73, 883) were heated at 190° C. for 17 h. The crude reaction was chromatographed on silica gel with ethyl acetate/hexane (1:6) then ethyl acetate/hexane (1:2) to give 4.4 g (75.5%) of the title compound. $^1$H-NMR (400 MHz, CDCl$_3$) δ$_H$ 1.96 (6H, s, CH$_3$), 3.75 (3H, s, OCH$_3$), 3.88 (3H, s, OCH$_3$), 6.54-7.83 (9H, ArH).

Step E: 7-methoxy-10-(4-methoxyphenyl)-5-methyl-phenanthrene-2-carbonitrile i. 6'-methyl-2'-bromomethyl-2-(4-methoxybenzoyl)-biphenyl-4-carbonitrile To a refluxing solution of the compound from Step D (45.5 g, 122 mmol) and AIBN (1.0 g) in CCl$_4$ (2.5 L) was added a mixture of NBS (23.0 g, 129 mmol) and AIBN (1.0 g) in ten equal portions. The reaction mixture was refluxed for 2 h after the addition of the last portion of NBS/AIBN. The reaction mixture was concentrated to approximately 1 L and washed 3 times with water (1 L). The organic layer was dried with anhydrous Na$_2$SO$_4$, filtered and the solvent removed. Toluene (200 ml) was added to the residue and then evaporated. Repeating this procedure gave 48 g of the title compound that was used without further purification.

ii. 5-methoxy-2-[2'-(4-methoxybenzoyl)-4'-cyanophenyl]-(3-methylbenzyl)-triphenylphosphonium bromide.

The crude mixture from i was dissolved in DMF (200 ml), triphenyphosphine (48 g) added and the reaction stirred at 100° C. for 5 h. The hot reaction mixture was slowly poured into vigorously stirring methyl t-butyl ether (4 L), stirred for an additional 30 min and filtered. The residue was washed twice with methyl t-butyl ether (200 ml) and immediately dissolved in CH$_2$Cl$_2$ (1 L).

iii. 7-methoxy-10-(4-methoxyphenyl)-5-methylphenanthrene-2-carbonitrile.

The crude product from ii was added over 5 h to a vigorously stirred mixture of CH$_2$Cl$_2$ (2 L) and 50% aqueous NaOH (1 L) at 35° C. Stirring was continued for an additional 3 h at 35-40° C. The organic layer was separated and washed consecutively with 1 N HCl (200 ml), water (200 ml), and saturated NaHCO$_3$ (200 ml). After drying the organic layer over anhydrous Na$_2$SO$_4$ and removing the solvent the residue was crystallized from CH$_2$Cl$_2$/hexanes/ethanol (80/60/10, 150 ml) to give 24 g of the title compound. The filtrated was concentrated and chromatographed on silica using CH$_2$Cl$_2$/hexanes (50/50) to give an additional 5.5 g (total 29.5 g, 68.5%) of the title compound. $^1$H-NMR (400 MHz, CDCl$_3$) δ$_H$ 3.12 (3H, s, CH$_3$), 3.94 (3H, s, OCH$_3$), 3.97 (3H, s, OCH$_3$), 7.07-8.94 (10H, ArH).

Step F: 1-[7-methoxy-10-(4-methoxyphenyl)-5-methylphenanthren-2-yl]-2-methyl-1-propan-1-one The compound from step E, iii (10.0 g, 28.3 mmol) was added to anhydrous THF (200 ml) and isopropyl magnesium chloride (2.0 M) in THF (15.6 ml) was added with stirring under Ar. After 10 min, crystalline CuBr (72 mg) was added and the reaction stirred for 9 h. TLC analysis indicated that there was still starting material present and an additional 8 ml of the Grignard reagent was added and the reaction stirred overnight. To the reaction was then added 10% H$_2$SO$_4$ (150 ml) and the mixture placed on a rotary evaporator to remove the THF. The remaining aqueous layer was stirred overnight at room temperature, extracted with CHCl$_3$ (3×250 ml) and washed with water (3×150 ml). After removing the CHCl$_3$ the residue was dried under high vacuum to yield 11.2 g (quantitative yield) of the title compound. $^1$H-NMR (400 MHz, CDCl$_3$) δ$_H$ 1.22 (6H, d, CH$_3$), 3.15 (3H, s, CH$_3$), 3.54 (1H, septet, COCH), 3.94 (3H, s, OCH$_3$), 3.96 (3H, s, OCH$_3$), 7.09-8.93 (10H, ArH).

Step G: 1-[7-hydroxy-10-(4-hydroxyphenyl)-5-methylphenanthren-2-yl]-2-methylpropan-1-one.

The compound from Step F (5.53 g, 13.9 mmol) and 48% HBr (44 ml) and acetic acid (55 ml) were heated (oil bath at 126° C.) in a closed thick walled pressure flask for 3.5 h. The reaction was then poured into water (300 ml) and extracted with ethyl acetate (3×250 ml). The combined extracts were then washed with water (3×150 ml). After removing the solvent, the residue was dried under high vacuum to yield the title compound quantitatively. $^1$H-NMR (400 MHz, DMSO-d$_6$) $\delta_H$ 1.10 (6H, d, CH$_3$), 3.03 (3H, s, CH$_3$), 3.56 (1 H, septet, COCH), 6.96-8.87 (10H, ArH), 9.65 (1H, br, OH), 10.1 (1H, br, OH).

Step H: 1-[7-hydroxy-5-methyl-10-[4-(2-piperidin-1-yl-ethoxy)-phenyl]-phenanthren-7-yl]-2-methyl-propan-1-one The compound from Step G (1.1 g, 3.0 mmol), aliquat (3.03 g, 7.5 mmol), NaOH (1.2 g, 30 mmol) and 1-(2-chloroethyl)piperidinium hydrochloride (0.552 g, 3.0 mmol) were added to TMU (70 ml) and heated at 50° C. for 11 h. The reaction mixture was added to water (500 ml), acidified with concentrated HCl (3 ml) and then neutralized with an excess of NaHCO$_3$ until pH 8. The reaction was extracted with ethyl acetate (3×250 ml) and the combined extracts washed with water (2×150 ml) and then concentrated. The residue was chromatographed on silica gel with acetone/hexane (1:2) to give 0.383 g (26.5%) of the title compound. $^1$H-NMR (400 MHz, CDCl$_3$) $\delta_H$ 1.15 (6H, d, CH$_3$), 1.53 (2H, br, NCH$_2$CH$_2$CH$_2$), 1.75 (4H, m, NCH$_2$CH$_2$CH$_2$), 2.71 (4H, br, NCH$_2$CH$_2$CH$_2$), 2.92 (2H, t, OCH$_2$CH$_2$N), 3.07 (3H, s, CH$_3$), 3.44 (1H, septet, COCH), 4.23 (2H, t, OCH$_2$CH$_2$N), 6.83-8.88 (10H, ArH).

EXAMPLE 3

ND72

Synthesis of 7-(1,2-dimethylpropenyl)-4-methyl-9-[4-(2-piperidin-1-yl-ethoxy)-phenyl]-phenanthren-2-ol Step A: (+) 7-(1-hydroxy-1,2-dimethylpropyl)-4-methyl-9-[4-(2-pyrrolidine-1-yl-ethoxy)-phenyl]-phenanthren-2-ol To the compound from Example 2, Step H (0.57 g, 1.2 mmol) was added methyl magnesium iodide (3 N) in THF (3.0 ml) and the mixture stirred overnight at room temperature. After removing the THF, CHCl$_3$ (50 ml) was added to the residue along with H$_2$SO$_4$ (0.675 g) dissolved in water (20 ml, pH 1). The residue completely dissolved. Excess NaHCO$_3$ was added and the organic layer separated, evaporated and dried under high vacuum to give the title compound in quantitative yield. $^1$H-NMR (400 MHz, CDCl$_3$) $\delta_H$ 0.77 (3H, d, CH$_3$), 0.83 (3H, d, CH$_3$), 1.47 (3H, s, CH$_3$), 1.53 (2H, m, NCH$_2$CH$_2$CH$_2$), 1.72 (4H, m, NCH$_2$CH$_2$CH$_2$), 2.01 (1H, septet, CH(CH$_3$)$_2$), 2.67 (4H, br, NCH$_2$CH$_2$CH$_2$), 2.90 (2H, t, OCH$_2$CH$_2$N), 3.09 (3H, s, CH$_3$), 4.21 (2H, t, OCH$_2$CH$_2$N), 6.88-8.80 (10H, ArH).

Step B: 7-(1,2-dimethylpropenyl)-4-methyl-9-[4-(2-piperidin-1-yl-ethoxy)-phenyl]-phenanthren-2-ol The compound from Step A (0.587 g, 1.2 mmol) was dissolved in glacial acetic acid (7.0 ml) and concentrated H$_2$SO$_4$ (1 drop) was added. The mixture was heated for 20 min at 75° C. with stirring. The reaction was neutralized with NaHCO$_3$ (10.5 g in 25 ml of water) and extracted with methyl t-butyl ether (3×25 ml), evaporated and dried under high vacuum. The residue was chromatographed on silica gel with acetone/hexane (1:2) to give 0.407 g (85%) of the title compound. $^1$H-NMR (400 MHz, CDCl$_3$) $\delta_H$ 0.77 (3H, d, CH$_3$), 0.83 (3H, d, CH$_3$), 1.47 (3H, s, CH$_3$), 1.55 (2H, m, NCH$_2$CH$_2$CH$_2$), 1.76 (4H, m, NCH$_2$CH$_2$CH$_2$), 2.72 (4H, br, NCH$_2$CH$_2$CH$_2$), 2.95 (2H, t, OCH$_2$CH$_2$N), 3.11 (3H, s, CH$_3$), 4.24 (2H, t, OCH$_2$CH$_2$N), 6.87-8.78 (10H, ArH).

EXAMPLE 4

ND75

Synthesis of 1-[7-hydroxy-5-methyl-10-[4-(2-piperidin-1-yl-ethoxy)-phenyl]-phenanthren-2-yl]-ethanone Step A: 1-[7-methoxy-10-(4-methoxyphenyl)-5-methylphenanthren-2-yl]-ethanone Following the procedure outlined in Example 2, Step F, 7-methoxy-10-(4-methoxyphenyl)-5-methylphenanthrene-2-carbonitrile (1.22 g, 3.46 mmol) and methyl magnesium bromide (3M) in diethyl ether (2.5 ml) were reacted to give 1.42 g (quantitative yield) of the title compound. $^1$H-NMR (400 MHz, CDCl$_3$) $\delta_H$ 2.61 (3H, s, CH$_3$), 3.15 (3H, s, COCH$_3$), 3.94 (3H, s, OCH$_3$), 3.97 (3H, s, OCH$_3$), 7.08-8.94 (10H, ArH).

Step B: 1-[7-hydroxy-10-(4-hydroxyphenyl)-5-methylphenanthren-2-yl]-ethanone

BBr$_3$ (100 ml, 1M in CH$_2$Cl$_2$) was added to the compound from Step A (6.76 g, 18.3 mmol) dissolved in CH$_2$Cl$_2$ (200 ml) at −60 to −70° C. The reaction was stirred overnight at −60 to 3° C. and then poured into water/ice (500 ml) and extracted with CHCl$_3$/Acetone (2.5 L, 5/1). After evaporating the solvent, the residue was chromatographed on silica gel using a gradient of ethyl acetate:methanol (95:5) to ethyl acetate: methanol (80:20) to give the title compound. $^1$H-NMR (400 MHz, DMSO-d$_6$) $\delta_H$2.16 (3H, s, CH$_3$), 2.67 (3H, s, COCH$_3$), 6.52-8.48 (10H, ArH), 8.81 (1H, br, OH), 9.91 (1H, br, OH).

Step C: 1-[7-hydroxy-5-methyl-10-[4-(2-piperidin-1-yl-ethoxy)-phenyl]-phenanthren-2-yl]-ethanone The compound for Step B (0.135 g, 0.394 mmol) was dissolved in anhydrous DMF (5 ml). NaH (75 mg, 60% in oil) was added and the reaction stirred for 10 min at room temperature. A solution of 1-(2-chloroethyl)-piperidine hydrochloride (75 mg, 0.40 mmol) in DMF (4.5 ml) was added slowly over 2 h. After the addition was complete the reaction was stirred for 2 h at 40-50° C. and then overnight at room temperature. The reaction mixture was added to water (50 ml), extracted with ethyl acetate (75 ml), dried, concentrated and chromatographed on silica using ethyl acetate:methanol (9:1) to give the title compound. $^1$H-NMR (400 MHz, CDCl$_3$) $\delta_H$ 1.53 (2H, br, NCH$_2$CH$_2$CH$_2$), 1.76 (4H, m, NCH$_2$CH$_2$CH$_2$), 2.51 (3H, s, COCH$_3$), 2.72 (4H, br, NCH$_2$CH$_2$CH$_2$), 2.93 (2H, t, OCH$_2$CH$_2$N), 3.10 (3H, s, CH$_3$), 4.24 (2H, t, OCH$_2$CH$_2$N), 6.83-8.87 (10H, ArH).

EXAMPLE 5

ND74

Synthesis of 7-isopropenyl-4-methyl-9-[4-(2-pyrrolidin-1-yl-ethoxy)-phenyl]-phenanthren-2-ol Step A: (+)-7-(1-hydroxy-1-methyl-ethyl)-4-methyl-9-[4-(2-pyrrolidin-1-yl-ethoxy)-phenyl]-phenanthren-2-ol The compound from Example 4, Step C (0.65 g, 1.4 mmol) in anhydrous THF (150 ml) was cooled to 0° C. Methyl magnesium bromide (3M) in diethyl ether (4.8 ml, 14 mmol) was added. The reaction was stirred overnight at 0° C., followed by the addition of cold 1N HCl (35 ml). Ethyl acetate (100 ml) was added and the aqueous phase saturated with Na$_2$CO$_3$ The organic layer was separated, dried and the solvent removed to yield a yellow, glassy residue (0.83 g) of the title compound that was used without further purification.

Step B: 7-Isopropenyl-4-methyl-9-[4-(2-pyrrolidin-1-yl-ethoxy)-phenyl]-phenanthren-2-ol The crude compound form Step A was dissolved in CH$_2$Cl$_2$ (20 ml), 10-camphorsulphonic acid (1 g) was added and the mixture refluxed for 1 h. After removing the solvent the residue was dissolved in ethyl acetate (100 ml) and a saturated solution of Na$_2$CO$_3$ (25 ml) was added and the mixture stirred for 15 min. The organic layer was separated, dried, concentrated and the residue chromatographed on silica gel using hexanes:acetone (60:40) to yield 0.412 g (65%) of the title compound. $^1$H-NMR (400 MHz, CDCl$_3$)

δ$_H$ 1.52 (2H, br, NCH$_2$CH$_2$CH$_2$), 1.75 (4H, m, NCH$_2$CH$_2$CH$_2$), 2.05 (3H, s, CH$_3$), 2.71 (4H, br, NCH$_2$CH$_2$CH$_2$), 2.92 (2H, t, OCH$_2$CH$_2$N), 3.10 (3H, s, CH$_3$), 4.24 (2H, t, OCH$_2$CH$_2$N), 5.05 (1H, s, =CH), 5.36 (1H, s, =CH), 6.84-8.78 (10H, ArH).

EXAMPLE 6

ND84

Synthesis of (+)-7-(1-hydroxyethyl)-4-methyl-9-[4-(2-pyrrolidin-1-yl-ethoxy)-phenyl]-phenanthren-2-ol The compound from Example 4, Step C (0.550 g, 1.2 mmol) was dissolved in methanol (45 ml). NaBH$_4$ (0.175 g, 4 eq.) was added in portions over 1 h at −5 to −3° C. The reaction was brought to room temperature and stirred for 2 h. The solvent was removed and water and ethyl acetate were added. The mixture was acidified to pH 2 with concentrated HCl and then excess Na$_2$CO$_3$ was added. The organic layer was separated and the aqueous layer extracted with ethyl acetate. The combined organic layers were washed with brine, dried and concentrated. The residue was chromatographed on silica with hexanes:acetone (1:1) to yield 0.447 g, (81%) of the title compound. $^1$H-NMR (400 MHz, CDCl$_3$) δ$_H$ 1.34 (3H, d, CH$_3$), 1.40 (2H, m, NCH$_2$CH$_2$CH$_2$), 1.52 (4H, m, NCH$_2$CH$_2$CH$_2$), 2.47 (3H, s, CH$_3$), 2.47 (4H, br, NCH$_2$CH$_2$CH$_2$), 2.71 (2H, t, OCH$_2$CH$_2$N), 3.01 (3H, s, CH$_3$), 4.16 (2H, t, OCH$_2$CH$_2$N), 4.79 (1H, dq, CH), 5.19 (1H, d, OH), 7.05-8.76 (10H, ArH), 9.75 (1H, s, OH).

EXAMPLE 7

ND90

Synthesis of 7-ethyl-4-methyl-9-[4-(2-pyrrolidin-1-yl-ethoxy)-phenyl]-phenanthren-2-ol The compound from Example 4, Step C (0.091 g, 0.2 mmol) was dissolved in dry THF (5 ml). Liquid NH$_3$ (6 ml) was added via a cannula at −78° C. Lithium (4 mg) was then added and the reaction stirred for 30 min.

Additional Li (10 mg) was added and the reaction stirred for an additional 1 h. The reaction was quenched with solid NH$_4$Cl (3.3 g). The NH$_3$ was allowed to boil off and the residue partitioned between CH$_2$Cl$_2$ and water. The water layer was separated, extracted with CH$_2$Cl$_2$ and the combined organic layers dried, concentrated and chromatographed on silica gel using a gradient of methanol:CH$_2$Cl$_2$ (5:95 to 30:70) to give 0.035 g (40%) of the title compound. $^1$H-NMR (400 MHz, CDCl$_3$) δ$_H$ 1.16 (3H, t, CH$_3$), 1.47 (2H, m, NCH$_2$CH$_2$CH$_2$), 1.67 (4H, m, NCH$_2$CH$_2$CH$_2$), 2.54 (2H, q, CH$_2$), 2.55 (3H, s, CH$_3$), 2.56 (4H, br, NCH$_2$CH$_2$CH$_2$), 2.82 (2H, t, OCH$_2$CH$_2$N), 2.87 (1H, dd, ArCH), 3.00 (1H, dd, ArCH) 3.92 (1H, dd, ArCHAr), 4.10 (2H, m, OCH$_2$CH$_2$N), 6.50-7.56 (9H, ArH).

EXAMPLE 8

ND80

Synthesis of 1-[7-hydroxy-10-[4-(2-piperidin-1-yl-ethoxy)-phenyl]-phenanthren-2-yl]-ethanone
Step A: 4-methoxy-2-methyl-benzaldehyde 3-methyl-anisole (36.6 g, 300 mmol) was reacted as described in Example 2 (Step A) to give 41.8 g (93%) of the title compound. $^1$H-NMR (400 MHz, CDCl$_3$) δ$_H$2.65 (3H, s, CH$_3$), 3.87 (3H, s, OCH$_3$), 6.74 (1H, d, ArH), 6.85 (1H, dd, ArH), 7.76 (1H, d, ArH), 10.11 (1H, s, CHO).

Step B: 3-(4-methoxy-2-methylphenyl)-1-(4-methoxyphenyl)-propenone

The compound from Step A (41.8 g, 279 mmol) was reacted as described in Example 2 (Step B) to give 51 g (65%) of the title compound. $^1$H-NMR (400 MHz, CDCl$_3$) δ$_H$2.48 (3H, s, CH$_3$), 3.85 (3H, s, OCH$_3$), 3.90 (3H, s OCH$_3$), 6.76-6.82 (2H, s, ArH), 6.99 (2H, d, ArH), 7.40, (1H, d, COCH), 7.70 (1H, d, ArH), 8.08 (1H, d, ArCH),8.50 (2H, d, ArH).

Step C: 3-(4-methoxy-2-methylphenyl)-1-(4-methoxy-phenyl)-propynone
 i. 2,3-dibromo-3-(4-methoxy-2-methylphenyl)-1-(4-methoxy-phenyl)-propan-1-one.

The compound from Step B (51.0 g, 182 mmol) was reacted as described in Example 2 (Step C) to give the title compound that was used without further purification. $^1$H-NMR (400 MHz, CDCl$_3$) δ$_H$2.48 (3H, s, CH$_3$), 3.84 (3H, s, OCH$_3$), 3.92 (3H, s, OCH$_3$), 5.90 (1H, d, ArCHBr), 6.00 (1H, d, COCHBr), 6.74 (1H, d, ArH), 6.88 (1H, dd, ArH), 7.03 (2H, d, ArH), 7.54 (1H, d, ArH), 8.07 (2H, d, ArH).
 ii. acetic acid, 2-bromo-1-(4-methoxy-2-methylphenyl-)-3-(4-methoxyphenyl)-3-oxo-propyl ester.

The crude compound from step i was reacted as described in Example 2 (Part C) to give 79 g of the title compound that was used without further purification. $^1$H-NMR (400 MHz, CDCl$_3$) δ$_H$ 1.88 (3H, s, COCH$_3$), 2.60 (3H, s, CH$_3$), 3.81 (3H, s, OCH$_3$), 3.91 (3H, s, OCH$_3$), 5.36 (1H, d, COCHBr), 6.60 (1H, d, COCHAr), 6.36 (1H, d, ArH), 6.81 (1H, dd, ArH), 7.00 (2H, d, ArH), 7.35 (1H, d, ArH), 8.05 (2H, d, ArH).
 iii. 3-(4-methoxy-2-methylphenyl)-1-(4-methoxyphenyl)-propynone.

The crude compound from step ii was reacted as described in Example 2 (Part C) to give 13 g (26%) of the title compound. $^1$H-NMR (400 MHz, CDCl$_3$) δ$_H$2.59 (3H, s, CH$_3$), 3.85 (3H, s, OCH$_3$), 3.91 (3H, s, OCH$_3$), 6.82-8.21 (7H, ArH).
Step D: 4'-methoxy-2'-methyl-2-(4-methoxybenzoyl)-biphenyl-4-carbonitrile The compound from Step C, iii (5.61 g, 20.0 mmol) was reacted as described in Example 2 (Part D) to give the title compound in quantitative yield. $^1$H-NMR (400 MHz, CDCl$_3$) δ$_H$2.14 (3H, s, CH$_3$), 3.74 (3H, s, OCH$_3$), 3.84 (3H, s, OCH$_3$), 6.56-7.79 (10H, ArH).
Step E: 7-methoxy-10-(4-methoxy-phenyl)-phenanthrene-2-carbonitrile
 i. 2'-bromo-methyl-2-(4-methoxy-benzoyl)-biphenyl-4-carbonitrile.

The compound from Step D (4.6 g, 13 mmol) was reacted as described in Example 2 (Part E) to give the title compound that was used without further purification.
 ii. 5-methoxy-2-[2'-(4-methoxy-benzoyl)-4'-cyanophenyl]-benzyl-triphenylphosphonium bromide.

The crude mixture from i was reacted as described in Example 2 (Part E) to give the title compound that was used without further purification.
 iii. 7-methoxy-10-(4-methoxy-phenyl)-phenanthrene-2-carbonitrile.

The crude product from ii was reacted as described in Example 2 (Part E) to give 2.8 g (64%) of the title compound. $^1$H-NMR (400 MHz, CDCl$_3$) δ$_H$3.94 (3H, s, OCH$_3$), 3.99 (3H, s, OCH$_3$), 7.08-8.73 (11H, ArH).
Step F: 1-[7-methoxy-10-(4-methoxy-phenyl)-phenanthren-2-yl]-ethanone The compound from step E, iii (2.8 g, 8.3 mmol) and methyl magnesium bromide (3M) in diethyl ether (6.1 ml, 18 mmol) were reacted as described in Example 2 (Part F)

to give the title compound. $^1$H-NMR (400 MHz, CDCl$_3$) $\delta_H$2.61 (3H, s, COC$\underline{H}_3$) 3.94 (3H, s, OCH$_3$), 3.99 (3H, s, OCH$_3$), 7.07-8.73 (11H, ArH).

Step G: 1-[7-hydroxy-10-(4-hydroxyphenyl)-phenanthren-2-yl]-ethanone

The compound from Step F was reacted as described in Example 2 (Part G) to give the title compound. $^1$H-NMR (400 MHz, DMSO-d$_6$) $\delta_H$2.59 (3H, s, COCH$_3$), 6.95-8.87 (11H, ArH), 9.7 (1H, br, OH), 10.1 (1H, br, OH).

Step H: 1-[7-hydroxy-10-[4-(2-piperidin-1-yl-ethoxy)-phenyl]-phenanthren-7-yl]-ethanone The compound from Step G (1.35 g, 4.12 mmol) was reacted as described in Example 2 (Part H) to give 0.175 g (9.7%) of the title compound. $^1$H-NMR (400 MHz, DMSO-d$_6$) $\delta_H$ 1.40 (2H, br, NCH$_2$CH$_2$C$\underline{H}_2$), 1.53 (4H, m, NCH$_2$C$\underline{H}_2$CH$_2$), 2.49 (4H, br, NC$\underline{H}_2$CH$_2$CH$_2$), 2.57 (3H, s, CH$_3$), 2.70 (2H, t, OCH$_2$C$\underline{H}_2$N), 4.16 (2H, t, OC$\underline{H}_2$CH$_2$N), 7.11-8.86 ( 11H, ArH), 10.12 (1H, br, OH).

EXAMPLE 9

Effectiveness of Compounds of Formula 3 and 4 at Inhibiting MCF-7 Cell Proliferation Those skilled in the art will appreciate that several acceptable estrogen receptor-binding assays are known and available for initial screening of the compounds of the present invention. The initial screen chosen was a human cell line assay, namely the MCF-7 cell proliferation assay for detecting anti-estrogenic/estrogenic activity. The MCF-7 human breast cancer cell line has been used as an industry standard for the evaluation of estrogen receptor antagonists. MCF-7 cells are estrogen-receptor positive (ER+) cancer cells that respond to estradiol stimulation. Antiestrogenic activity is measured in terms of a test article's ability to inhibit estradiol stimulated proliferation, implying an antagonistic action on the estrogen receptor and estogenic activity can be inferred from increased proliferation. The following testing procedure was used.

MCF-7 cells were maintained in RPMI medium free of phenol red and supplemented with 5% charcoal-stripped foetal calf serum, hydrocortisone, bovine insulin, penicillin and streptomycin until they reached 70% confluence. The cells were kept in a 5% CO$_2$ atmosphere and prior to treatment were washed twice with Ca$^{++}$/Mg$^{++}$ free Hanks balanced salt solution and harvested with 1 mM EDTA prepared in Ca$^{++}$/Mg$^{++}$ free Hanks balanced salt solution. After the washes the cells were re-suspended in medium. Cells were seeded in 96-well plates and incubated for 16 hours in 5% charcoal-stripped calf serum phenol red-free medium. Cells were then treated continuously with estradiol, a test article, or a combination of both using various serum concentrations. Cell survival was evaluated after 3-6 days, by replacing the culture media with 150 $\mu$l of fresh medium containing 10 mM 4-(2-hydroxyethyl)-1-piperazineethamsulfonic acid buffer (pH 7.4) followed by addition of 50 $\mu$l of 2.5 mg/ml of 3-(4,5-dimethylthiazo-2-yl)-2,5-diphenyltetrazolium bromide (MTT). After 4 hours of incubation at 37° C. the medium and MTT were removed and 200 $\mu$l of dimethylsulfoxide (DMSO) was added to dissolve the precipitate of reduced MTT, followed by addition of 25 $\mu$l of glycine buffer (0.1M glycine plus 0.1M NaCl, pH 10.5). Plates were shaken for 15 minutes and the absorbance was determined at 570 nm with a microplate reader (BIORAD, model 450). Data are expressed as percent (%) cell growth in comparison with untreated cells.

FIGS. 1 and 2 show the dose-response curves of estradiol stimulated versus unstimulated MCF-7 cells in the presence of the compounds depicted by Formula 3 and Formula 4 respectively. The shifts of the response curves indicate that the test compounds are antagonizing the effect of estradiol on these cells. This is a positive indication that the compounds of the present invention are of potential in the treatment of a wide variety of disease states involving the estrogen receptor.

EXAMPLE 10

Effectiveness of Compounds of Formulas 3, 5, 6 and 7 at Displacing Estrogen ER-alpha and ER-beta in Human Recombinant Estrogen Receptors The human estrogen receptor occurs in two subtypes, alpha and beta. The stable expression of these individual receptor subtypes in cells provides a rapid and accurate means of quantifying the direct interaction of a test article with the estrogen binding sites. Briefly, this assay is conducted in 96 well plates where a series of concentrations of test article are used to displace tritiated estradiol from either estrogen receptor alpha or estrogen receptor beta bearing cell membranes, under equilibrium conditions. The measurement of the displaced tritiated estradiol allows the determination of an IC$_{50}$ value (concentration of test article that inhibits 50% of the estradiol binding). This measurement is the primary test for mediation of the estrogen receptor and can also be used to measure the relative selectivity of the test article for either the alpha or beta subtype.

The alpha subtype assay measures the binding of [$^3$H] Estradiol to the human recombinant estrogen receptor. The receptor preparation was obtained from PanVera Corporation and used in an assay that followed the method taught by Obourn (Obourn et al., *Biochemistry* 1993; 32:6229–6236) with some minor variations. Briefly, after proper dilution, a 4.5 ng aliquot of receptor protein in modified Tris-HCL pH 7.5 buffer is incubated with 0.5 nM [$^3$H] Estradiol for 2 hours at 25° C. Non-specific binding is estimated in the presence of 1.0 $\mu$M diethylstilbestrol. Membranes are filtered and washed 3 times, and the filters are counted to determine [$^3$H] Estradiol specifically bound. Under the same conditions the receptor protein is incubated with varied concentrations of test article ranging from 1 nM to 1 $\mu$M and the displacement of [$^3$H] Estradiol is measured in duplicate. The measurement of the displaced tritiated estradiol allows the determination of an IC$_{50}$ value, a direct measure of the test articles interaction with the estrogen receptor alpha.

The beta subtype assay also allowed the determination of an IC$_{50}$ value of the test article under the same conditions as for the alpha subtype assay with the exception that a 7.5 ng aliquot of receptor protein preparation was used.

Table 1 shows the IC$_{50}$ results of the compounds depicted by Formula 3, 5, 6 and 7. The IC$_{50}$ values are both below 100 $\mu$M range. This is an indication of very high binding affinity for the estrogen receptor with a slight preference for the alpha subtype and of the potential of the class of compounds represented by formula I in the treatment of disease states involving the estrogen receptor.

TABLE 1

| Estrogen Receptor Binding Assay Results | | |
|---|---|---|
| Compound | ER Subtype | IC$_{50}$ Value |
| formula 3 | Alpha | 0.039 $\mu$M |
|  | Beta | 0.120 $\mu$M |

TABLE 1-continued

Estrogen Receptor Binding Assay Results

| Compound | ER Subtype | IC$_{50}$ Value |
|---|---|---|
| formula 5 | Alpha | 0.032 µM |
|  | Beta | 0.020 µM |
| formula 6 | Alpha | 0.018 µM |
|  | Beta | 0.009 µM |
| formula 7 | Alpha | 0.165 µM |
|  | Beta | 0.094 µM |

The terms and descriptions used herein are preferred embodiments set forth by way of illustration only, and are not intended as limitations on the many variations which those of skill in the art will recognize to be possible in practicing the present invention. It is the intention that all possible variants whether presently known or unknown, that do not have a direct and material effect upon the way the invention works, are to be covered by the following claims.

REFERENCES

Anstead G M, Carlson K E, Katzenellenbogen J A. The estradiol pharmacophore: Ligand structure-estrogen receptor binding affinity relationships and a model for the receptor binding site. *Steroids* 1997; 62:268–303.

Biegnon et al. U.S. Pat. No. 5,650,425 July 1997

Cameron et al. U.S. Pat. No. 5,552,412 September 1996

DeFriend D J, Howell A, Nicholson R I et al. Investigation of a new pure antiestrogen (ICI 182780) in women with primary breast cancer. *Cancer Res.* 1994; 54:408–15.

Draper U.S. Pat. No. 5,641,790 June 1997

Edwards et al. U.S. Pat. No. 5,589,500 December 1996

England G M, Jordan V C. Pure antiestrogens as a new therapy for breast cancer. *Oncol. Res.* 1997; 9:397–402.

EP 0 818 453 A1 June 1997 European Pat. Off.

Fisher B. et al. "Tamoxifen for Prevention of Breast Cancer: Report of the National Surgical Adjuvant Breast and Bowel Project P-1 Study" *J. of the Nat'l. Cancer Inst.* 1998; Vol. 90; No. 18; 1371–1388.

Gradishar W J, Jordan C V. Clinical potential of new anti-estrogens. *J. Clin. Oncol.* 1997; 15(2):840–52.

Grese T A, Pennington L D, Sluka J P et al. Synthesis and pharmacology of conformationally restricted raloxifene analogues: highly potent selective estrogen receptor modulators. *J. Med. Chem.* 1998; 41:1272–83.

Grundy J. Artificial Estrogens. *Chem. Rev.* 1957; 57:281–416.

Howell A, DeFriend D, Robertson J, Blamey R, Walton P. Response to a specific anti-estrogen (ICI 182780) in tamoxifen-resistant breast cancer. *Lancet* 1995; 345:29–30.

Jordan V C, Murphy C S. Endocrine pharmacology of anti-estrogens as antitumor agents. *Endocr. Rev.* 1990; 11(4): 578–610.

Josefson D. Breast cancer trial stopped early. *Br. Med. J.* 1998; 316:1187.

| Labrie e al. | 5,631,249 | 05/1997 |
| Labrie et al. | 5,393,785 | 02/1995 |
| Labrie et al. | 5,395,842 | 03/1995 |
| Labrie et al. | 5,686,465 | 11/1997 |

Labudde J. A. and Heidelberger C. *J. Am. Chem. Soc.* 1958; 80:1225–1236.

Lerner L J, Jordan V C. Development of anti-estrogens and their use in breast cancer: Eighth Cain memorial award lecture. *Cancer Res.* 1990; 50:4177–89.

Levenson A S and Jordan V C. The key to the anti-estrogenic mechanism of raloxifene is amino acid 351 (Aspartate) in the estrogen receptor. *Cancer Res.* 1998; 58:1872–75

McDonnell D P, Dana S L, Hoener P A, Lieberman B A, Imhof M O, Stein R B. Cellular mechanisms which distinguish between hormone- and antihormone-activated estrogen receptor. *Ann. N. Y. Acad. Sci.* 1996; 121–37.

Mitlak B H, Cohen F J. In search of optimal long-term female hormone replacement: The potential of selective estrogen receptor modulators. *Horm. Res.* 1997; 48:155–63.

Nicholson R I, Gee J M W, Bryant S et al. Pure anti-estrogens: the most important advance in the endocrine therapy of breast cancer since 1986? *Ann. N. Y. Acad. Sci.* 1996; 784:325–35.

Nicholson R I. Anti-estrogens and breast cancer therapy. Pharmacology and Clinical Uses of Inhibitors of Hormone Secretion and Action. Bailliere Tindall, 1987:60–87.

Parczyk K, Schneider M R. The future of antihormone therapy: Innovations based on an established principle. *J. Cancer Res. Clin. Oncol.* 1996; 122:383–96.

Powles T J. Efficacy of tamoxifen as treatment of breast cancer. *Semin. Oncol.* 1997; 24(1):SI-48-SI-54.

Rauschning W, Pritchard K I. Droloxifene, a new anti-estrogen: its role in metastatic breast cancer. *Breast Cancer Res. Treat.* 1994; 31:83–94.

Schneider U.S. Pat. No. 5,733,902 March 1998

Wakeling A E, Bowler J. Biology and mode of action of pure anti-estrogens. *Journal of Steroid Biochemistry* 1988; 30(1-6):141–7.

Wakeling A E, Bowler J. ICI 182,780, A new anti-estrogen with clinical potential. *J. Steroid Biochem. Mol. Biol.* 1992; 43:1–3.

Wakeling A E, Bowler J. Novel anti-estrogens without partial agonist activity. *Journal of Steroid Biochemistry* 1988; 31(4B):645–53.

Wakeling A E, Bowler J. Steroidal pure anti-estrogens. *J. Endocrinol.* 1987; 112:R7–R10.

Wakeling A E, Dukes M, Bowler J. A potent specific pure anti-estrogen with clinical potential. *Cancer Res.* 1991; 51:3867–73.

Wakeling A E. The future of new pure anti-estrogens in clinical breast cancer. *Breast Cancer Res. Treat.* 1993; 25:1–9.

Wakeling A E. Therapeutic potential of pure anti-estrogens in the treatment of breast cancer. *J. Steroid Biochem. Mol. Biol.* 1990; 37(6):771–5.

Willson U.S. Pat. No. 5,681,835 October 1997

What is claimed is:

1. A compound of Formula 1 comprising A, B, C and D rings, or a pharmaceutically acceptable salt or ester thereof,

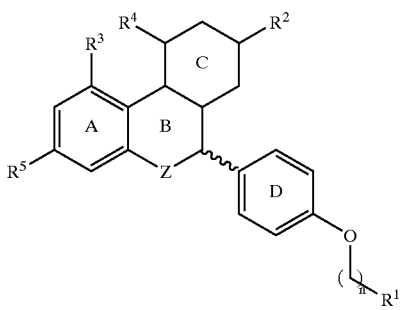

Formula 1 wherein:
i) $R^1$ represents a substituent selected from the group consisting of: 1-pyrrolidinyl, 1-piperidinyl methyl-1-pyrrolidinyl, dimethyl-1-pyrrolidino, 4-morpholino, dimethylamino, diethylamino, diisopropylamino and 1-hexamethyleneimino;
ii) $R^2$ represents a substituent selected from the group consisting of: $CH_2CH_2CH_3$, $CH_2C(CH_3)_2H$, $CH(OH)CH_2CH_3$, $CH=CHCH_3$, $CH=CHCH(CH_3)_2$, $CH_3C=CH_2$, $C=OCH_3$, $C=OCH_2CH_3$, $C=OCH(CH_3)_2$, $C=OCH=CH_2$, $C=OCH=C(CH_3)H$, $C=OCH=C(CH_3)_2$, $C(CH_3)=C(CH_3)_2$ and $CH(OH)CH_3$;
iii) $R^3$ is a hydrogen atom or a methyl group;
iv) $R^4$ is a hydrogen atom or a methyl group;
v) $R^5$ is a hydroxy group or an ester group represented by the formula ($OC=OCH_3$);
vi) "n" is an integer from 1 to 4 and
vii) "z" is a carbon atom, an oxygen atom or a sulfur atom.

2. The compound of claim 1, wherein;
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^2$ represents a substituent selected from the group consisting of $CH_2CH_2CH_3$, $CH_2C(CH_3)_2H$, $CH(OH)CH_2CH_3$, $CH=CHCH_3$, $CH=CHCH(CH_3)_2$, $CH_3C=CH_2$, $C=OCH_3$, $C=OCH_2CH_3$, $C=OCH(CH_3)_2$, $C=OCH=CH_2$, $C=OCH=C(CH_3)H$, $C=OCH=C(CH_3)_2$, $C(CH_3)=C(CH_3)_2$ and $CH(OH)CH_3$;
iii) $R^3$ is a hydrogen atom or a methyl group;
iv) $R^4$ is a hydrogen atom or a methyl group;
v) $R^5$ is a hydroxy group;
vi) "n" is an integer from 1 to 4 and
vii) "z" is a carbon atom, an oxygen atom or a sulfur atom.

3. The compound of claim 1, wherein;
i) $R^1$ represents a substituent selected from the group consisting of 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^2$ represents a substituent selected from the group consisting of; $CH_2CH_2CH_3$, $CH_2C(CH_3)_2H$, $CH(OH)CH_2CH_3$, $CH=CHCH_3$, $CH=CHCH(CH_3)_2$, $CH_3C=CH_2$, $C=OCH_3$, $C=OCH_2CH_3$, $C=OCH(CH_3)_2$, $C=OCH=CH_2$, $C=OCH=C(CH_3)H$, $C=OCH=C(CH_3)_2$, $C(CH_3)=C(CH_3)_2$ and $CH(OH)CH_3$;
iii) $R^3$ is a hydrogen atom or a methyl group;
iv) $R^4$ is a hydrogen atom or a methyl group;
v) $R^5$ is an ester group represented by the formula ($OC=OCH_3$);
vi) "n" is an integer from 1 to 4 and
vii) "z" is a carbon atom, an oxygen atom or a sulfur atom.

4. The compound of claim 1, wherein:
i) "z" is a carbon atom and
ii) at least one of said B-ring and C-ring is aromatic.

5. The compound of claim 1, wherein:
i) "z" is an oxygen atom;
ii) said B-ring is non-aromatic and
iii) said C-ring is aromatic or non-aromatic.

6. The compound of claim 1, wherein:
i) "z" is a sulfur atom;
ii) said B-ring is non-aromatic and
iii) said C-ring is aromatic or non-aromatic.

7. The compound of claim 1 wherein:
i) $R^1$ is a piperidinyl group;
ii) $R^2$ represents a substituent selected from the group consisting of: $C=O CH(CH_3)_2$, $C=OCH_3$, $CH_3C=CH_2$, $C(CH_3)=C(CH_3)_2$, $CH(OH)CH_3$;
iii) $R^3$ is a methyl group;
iv) $R^4$ is a hydrogen atom;
v) $R^5$ is a hydroxy group;
vi) "z" is a carbon atom and the B-ring and the C-ring are aromatic; and
vii) "n"=2.

8. A process for the preparation of a compound of Formula 1 comprising A, B, C and D rings or a pharmaceutically acceptable salt thereof, wherein:
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^2$ represents a substituent selected from the group consisting of:, $C=OCH_3$, $C=OCH_2CH_3$, $C=OCH(CH_3)_2$, $C=OCH=CH_2$, $C=OCH=C(CH_3)H$, and $C=OCH=C(CH_3)_2$;
iii) $R^3$ is a hydrogen atom or a methyl group;
iv) $R^4$ is a hydrogen atom or a methyl group;
v) "n" is an integer from 1 to 4;
vi) said B-ring is non-aromatic;
vii) said C-ring is aromatic; and
viii) said "z" is an oxygen atom
said process comprising:
a) reacting a molecule of Formula 1-8 comprising A, B, C and D rings:

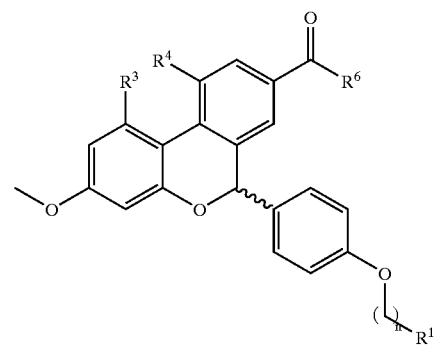

Formula 1-8 wherein:
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^6$ represents a substituent selected from the group consisting of: $CH_3$, $CH_2CH_3$, $CH(CH_3)_2$, $CH=CH_2$, $CH=CHCH_3$, and $CH=C(CH_3)_2$;
iii) $R^3$ is a hydrogen atom or a methyl group;
iv) $R^4$ is a hydrogen atom or a methyl group;
v) "n" is an integer from 1 to 4;
vi) said B-ring is non-aromatic and
vii) said C-ring is aromatic;
with either $BBr_3$ or concentrated HBr, thereby generating a reaction mixture and
b) recovering said compound of Formula 1 from said reaction mixture.

9. A process for the preparation of a compound of Formula 1 comprising A, B, C and D rings or a pharmaceutically acceptable salt thereof; wherein:
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^2$ represents a substituent selected from the group consisting of:, $C=OCH_3$, $C=OCH_2CH_3$, $C=OCH(CH_3)_2$, $C=OCH=CH_2$, $C=OCH=C(CH_3)H$, and $C=OCH=C(CH_3)_2$;
iii) $R^3$ is a hydrogen atom or a methyl group;
iv) $R^4$ is a hydrogen atom or a methyl group;
v) said B-ring and C-ring are aromatic; and
vi) said "z" is a carbon atom
said process comprising:
a) reacting a molecule of Formula 2-7 comprising A, B, C and D rings:

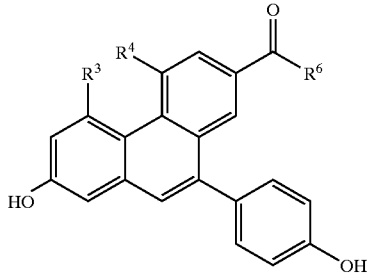

Formula 2-7 wherein:
ii) $R^6$ represents a substituent selected from the group consisting of: $CH_3$, $CH_2CH_3$, $CH(CH_3)_2$, $CH=CH_2$, $CH=CHCH_3$, and $CH=(CH_3)_2$;
iii) $R^3$ is a hydrogen atom or a methyl group;
iv) $R^4$ is a hydrogen atom or a methyl group; and
v) said B-ring and C-ring are aromatic;
with a reagent having the general formula $Cl(CH_2)_nR^1$ thereby generating a reaction mixture and wherein:
i) "n" is an integer for 1 to 4 and
ii) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;

b) recovering said compound of Formula 1 from said reaction mixture.

10. A process for the preparation of a non-steroidal estrogen receptor modulator of Formula 1 comprising A, B, C and D rings or a pharmaceutically acceptable salt thereof, wherein:
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^2$ represents a substituent selected from the group consisting of:, $C=OCH_3$, $C=OCH_2CH_3$, $C=OCH(CH_3)_2$, $C=OCH=CH_2$, $C=OCH=C(CH_3)H$, and $C=OCH=C(CH_3)_2$;
iii) $R^3$ is a hydrogen atom or a methyl group;
iv) $R^4$ is a hydrogen atom or a methyl group;
v) "n" is an integer from 1 to 4;
vi) said B-ring is non-aromatic;
vii) said C-ring is aromatic;
viii) said "z" is an oxygen atom;
said process comprising:
a) reacting a molecule of formula 1-8 comprising A, B, C and D rings:

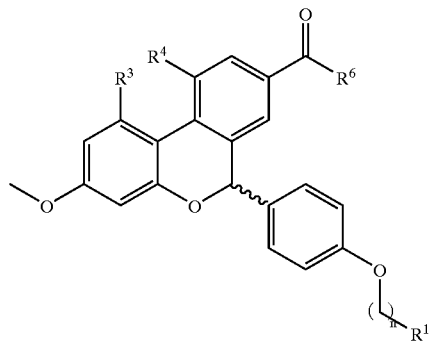

Formula 1-8 wherein:
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;
ii) $R^6$ represents a substituent selected from the group consisting of: $CH_3$, $CH_2CH_3$, $CH(CH_3)_2$, $CH=CH_2$, $CH=CHCH_3$, and $CH=C(CH_3)_2$;
iii) $R^3$ is a hydrogen atom or a methyl group;
iv) $R^4$ is a hydrogen atom or a methyl group;
v) "n" is an integer from 1 to 4;
vi) said B-ring is non-aromatic and
vii) said C-ring is aromatic;
with either $BBr_3$ or concentrated HBr, thereby generating a reaction mixture and
b) recovering said non-steroidal estrogen receptor of Formula 1 from said reaction mixture.

11. A process for the preparation of a non-steroidal estrogen receptor modulator of Formula 1 comprising A, B, C and D rings or a pharmaceutically acceptable salt thereof, wherein:
i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;

ii) $R^2$ represents a substituent selected from the group consisting of:, C=OCH$_3$, C=OCH$_2$CH$_3$, C=OCH(CH$_3$)$_2$, C=OCH=CH$_2$, C=OCH=C(CH$_3$)H, and C=OCH=C(CH$_3$)$_2$;

iii) $R^3$ is a hydrogen atom or a methyl group;

iv) $R^4$ is a hydrogen atom or a methyl group;

v) said B-ring and C-ring are aromatic; and vi) "z" is a carbon atom;

said process comprising:

a) reacting a molecule of Formula 2-7 comprising A, B, C and D rings:

Formula 2-7

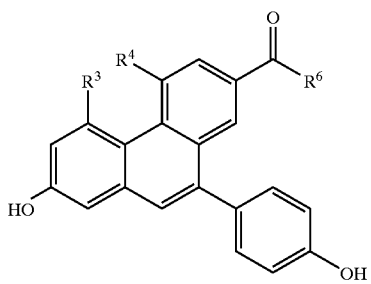

wherein:

ii) $R^6$ represents a substituent selected from the group consisting of: CH$_3$, CH$_2$CH$_3$, CH(CH$_3$)$_2$, CH=CH$_2$, CH=CHCH$_3$, and CH=C(CH$_3$)$_2$;

iii) $R^3$ is a hydrogen atom or a methyl group;

iv) $R^4$ is a hydrogen atom or a methyl group; and v) said B-ring and C-ring are aromatic;

with a reagent having the general formula Cl(CH$_2$)$_n$R$^1$ thereby generating a reaction mixture and wherein:

i) "n" is an integer for 1 to 4 and ii) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;

b) recovering said non-steroidal estrogen receptor of Formula 1 from said reaction mixture.

12. The process of claim 10, wherein said non-steroidal estrogen receptor modulator has the general Formula 1 comprising A, B, C and D rings, Formula 1

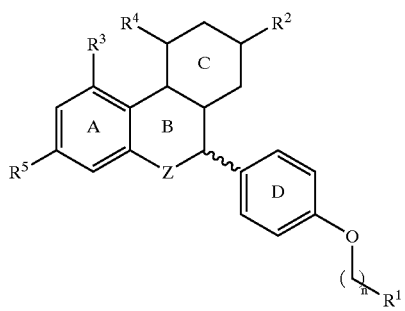

wherein:

i) $R^1$ represents a substituent selected from the group consisting of: 1-pyrrolidinyl, 1-piperidinyl, methyl-1-pyrrolidinyl, dimethyl-1-pyrrolidmo, 4-morpholino, dimethylamino, diethylamino, diisopropylamino and 1-hexamethyleneimino;

ii) $R^2$ represents a substituent selected from the group consisting of: CH$_2$CH$_2$CH$_3$, CH$_2$C(CH$_3$)$_2$H, CH(OH)CH$_2$CH$_3$, CH=CHCH$_3$, CH=CHCH(CH$_3$)2, CH$_3$C=CH$_2$, C=OCH$_3$, C=OCH$_2$CH$_3$, C=OCH(CH$_3$)$_2$, C=OCH=CH$_2$, C=OCH=C(CH$_3$)H, C=OCH=C(CH$_3$)$_2$, C(CH$_3$)C(CH$_3$)$_2$ and CH(OH)CH$_3$;

iii) $R^3$ is a hydrogen atom or a methyl group;

iv) $R^4$ is a hydrogen atom or a methyl group;

v) $R^5$ is a hydroxy group or an ester group represented by the formula (OC=OCH$_3$);

vi) "n" is an integer from 1 to 4 and vii) "z" is a carbon atom, an oxygen atom or a sulfur atom.

13. The non-steroidal estrogen receptor modulator of claim 12, wherein i) "z" is a carbon atom and ii) at least one of said B-ring and C-ring is aromatic.

14. The non-steroidal estrogen receptor modulator of claim 12, wherein:

i) "z" is an oxygen atom;

ii) said B-ring is non-aromatic and iii) said C-ring is aromatic or non-aromatic.

15. The non-steroidal estrogen receptor modulator of claim 12, wherein:

i) "z" is a sulfur atom;

ii) said B-ring is non-aromatic and iii) said C-ring is aromatic or non-aromatic.

16. The process of claim 11, wherein said non-steroidal estrogen receptor modulator has the general Formula 1 comprising A, B, C and D rings, Formula 1

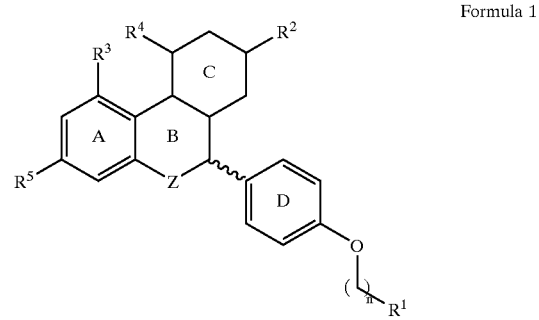

wherein:

i) $R^1$ represents a substituent selected from the group consisting of: 1-pyrrolidinyl, 1-piperidinyl, methyl-1-pyrrolidinyl, dimethyl-1-pyrrolidino, 4-morpholino, dimethylamino, diethylamino, diisopropylamino and 1-hexamethyleneimino;

ii) $R^2$ represents a substituent selected from the group consisting of: CH$_2$CH$_2$CH$_3$, CH$_2$C(CH$_3$)$_2$H, CH(OH)CH$_2$CH$_3$, CH=CHCH$_3$, CH=CHCH(CH$_3$)$_2$, CH$_3$C=CH$_2$, C=OCH$_3$, C=OCH$_2$CH$_3$, C=OCH(CH$_3$)$_2$, C=OCH=CH$_2$, C=OCH=C(CH$_3$)H, C=OCH=C(CH$_3$)$_2$, C(CH$_3$)=C(CH$_3$)$_2$ and CH(OH)CH$_3$;

iii) $R^3$ is a hydrogen atom or a methyl group;

iv) $R^4$ is a hydrogen atom or a methyl group;

v) $R^5$ is a hydroxy group or an ester group represented by the formula (OC=OCH$_3$);

vi) "n" is an integer from 1 to 4 and vii) "z" is a carbon atom, an oxygen atom or a sulfur atom.

17. A pharmaceutical composition comprising a therapeutically effective amount of the compound of claim 1 and at least one pharmaceutically acceptable carrier.

18. A pharmaceutical composition comprising a therapeutically effective amount of the compound of claim 2 and at least one pharmaceutically acceptable carrier.

19. A pharmaceutical composition comprising a therapeutically effective amount of the compound of claim 3 and at least one pharmaceutically acceptable carrier.

20. A pharmaceutical composition comprising a therapeutically effective amount of the compound of claim 4 and at least one pharmaceutically acceptable carrier.

21. A pharmaceutical composition comprising a therapeutically effective amount of the compound of claim 5 and at least one pharmaceutically acceptable carrier.

22. A pharmaceutical composition comprising a therapeutically effective amount of the compound of claim 6 and at least one pharmaceutically acceptable carrier.

\* \* \* \* \*

UNITED STATES PATENT AND TRADEMARK OFFICE
CERTIFICATE OF CORRECTION

PATENT NO.   : 6,599,921 B2
DATED        : July 29, 2003
INVENTOR(S)  : Schmidt et al.

It is certified that error appears in the above-identified patent and that said Letters Patent is hereby corrected as shown below:

Column 33,
Line 18, after "1-piperidinyl", insert -- , -- therefor.
Line 35, remove "vii) "2" is a carbon atom", and insert -- vii) "z" is a carbon atom -- therefor.
Lines 43 and 57, after "of", insert -- : -- therefor.

Column 34,
Line 39, remove "of:,", and insert -- of: -- therefor.

Column 35,
Line 28, remove "of:,", and insert -- of: -- therefor.

Column 37,
Line 4, remove "of:,", and insert -- of: -- therefor.

Column 38,
Line 6, remove "CH==CHCH(CH$_3$)2", and insert -- CH==CHCH(CH$_3$)$_2$ -- therefor.

Signed and Sealed this

Seventh Day of October, 2003

JAMES E. ROGAN
*Director of the United States Patent and Trademark Office*